(12) United States Patent
Moss et al.

(10) Patent No.: US 9,051,387 B2
(45) Date of Patent: Jun. 9, 2015

(54) INHIBITION OF MYBP-C BINDING TO MYOSIN AS A TREATMENT FOR HEART FAILURE

(71) Applicant: Wisconsin Alumni Research Foundation, Madison, WI (US)

(72) Inventors: Richard L. Moss, Madison, WI (US); Ariel Fernandez, Houston, TX (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/827,023

(22) Filed: Mar. 14, 2013

(65) Prior Publication Data

US 2013/0345135 A1 Dec. 26, 2013

Related U.S. Application Data

(60) Provisional application No. 61/663,200, filed on Jun. 22, 2012.

(51) Int. Cl.

| | |
|---|---|
| *A61K 38/17* | (2006.01) |
| *A61P 9/04* | (2006.01) |
| *A61K 38/08* | (2006.01) |
| *A61K 38/10* | (2006.01) |
| *A61K 45/06* | (2006.01) |
| *C07K 7/06* | (2006.01) |
| *C07K 7/08* | (2006.01) |
| *C07K 14/47* | (2006.01) |

(52) U.S. Cl.
CPC ......... *C07K 14/4716* (2013.01); *A61K 38/1719* (2013.01); *A61K 45/06* (2013.01); *A61K 38/08* (2013.01); *A61K 38/10* (2013.01)

(58) Field of Classification Search
None
See application file for complete search history.

(56) References Cited

U.S. PATENT DOCUMENTS

2013/0072549 A1* 3/2013 Stelzer .................. 514/44 R

FOREIGN PATENT DOCUMENTS

WO WO 2013/052933 4/2013

OTHER PUBLICATIONS

Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Phillips, A., J Pharm Pharmacology 53: 1169-1174, 2001.*
Vidal et al. 2005. European Journal of Cancer. 41: 2812-2818.*
Pirollo et al, 2008. Cancer Res. 68(5): 1247-1250.*

* cited by examiner

*Primary Examiner* — Zachary Howard
(74) *Attorney, Agent, or Firm* — Parker Highlander PLLC

(57) ABSTRACT

The present invention provides for methods of treating and slowing the onset of heart failure. The inventors have determined that myosin binding to unphosphorylated Myosin Binding Protein C (MyBP-C) plays a key role in the diminution of cardiac contractile force and frequency in heart failure. The present invention provides peptide inhibitors of the MyBP-C/myosin interaction, thereby increasing both cardiac contractile force and frequency in the failing heart, as well as in patients not yet exhibiting frank heart failure.

24 Claims, 6 Drawing Sheets

| | | |
|---|---|---|
| Full-length: | FSSLLKKRDÅFRRDAKLE (SEQ ID NO: 47) | 302A (18-mer) |
| Truncated: | SLLKKRDÅFRRDAKLE (SEQ ID NO: 53) | 302A-[-2]$_N$ (16-mer) |
| | LKKRDÅFRRDAKLE (SEQ ID NO: 55) | 302A-[-4]$_N$ (14-mer) |
| | FSSLLKKRDÅFRRDAK (SEQ ID NO: 56) | 302A-[-2]$_C$ (16-mer) |
| | FSSLLKKRDÅFRRD (SEQ ID NO: 57) | 302A-[-4]$_C$ (14-mer) |
| | LKKRDÅFRRD (SEQ ID NO: 58) | 302A-[-8] (10-mer) |
| Scrambled: | DALFKKAKSLRFELRSRD (SEQ ID NO: 59) | |

SEQUENCE LISTING

```
<160> NUMBER OF SEQ ID NOS: 59

<210> SEQ ID NO 1
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X is A, V or D

<400> SEQUENCE: 1

Leu Lys Lys Arg Asp Xaa Phe Arg Arg Asp
1               5                   10

<210> SEQ ID NO 2
<211> LENGTH: 34
<212> TYPE: PRT
<213> ORGANISM: Artificial Sequence
<220> FEATURE:
<223> OTHER INFORMATION: Synthetic peptide

<400> SEQUENCE: 2

Gln Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 3
<211> LENGTH: 16
<212> TYPE: PRT
<213> ORGANISM: Artificial Sequence
<220> FEATURE:
<223> OTHER INFORMATION: Synthetic peptide

<400> SEQUENCE: 3

Arg Gln Ile Lys Ile Trp Phe Gln Asn Arg Arg Met Lys Trp Lys Lys
1               5                   10                  15

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide
```

```
<400> SEQUENCE: 4

Arg Arg Met Lys Trp Lys Lys
1               5

<210> SEQ ID NO 5
<211> LENGTH: 16
<212> TYPE: PRT
<213> ORGANISM: Artificial Sequence
<220> FEATURE:
<223> OTHER INFORMATION: Synthetic peptide

<400> SEQUENCE: 5

Arg Arg Trp Arg Arg Trp Trp Arg Arg Trp Trp Arg Arg Trp Arg Arg
1               5                   10                  15

<210> SEQ ID NO 6
<211> LENGTH: 18
<212> TYPE: PRT
<213> ORGANISM: Artificial Sequence
<220> FEATURE:
<223> OTHER INFORMATION: Synthetic peptide

<400> SEQUENCE: 6

Arg Gly Gly Arg Leu Ser Tyr Ser Arg Arg Arg Phe Ser Thr Ser Thr
1               5                   10                  15

Gly Arg

<210> SEQ ID NO 7
<211> LENGTH: 11
<212> TYPE: PRT
<213> ORGANISM: Artificial Sequence
<220> FEATURE:
<223> OTHER INFORMATION: Synthetic peptide

<400> SEQUENCE: 7

Tyr Gly Arg Lys Lys Arg Arg Gln Arg Arg Arg
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

Arg Lys Lys Arg Arg Gln Arg Arg Arg
1               5

<210> SEQ ID NO 9
<211> LENGTH: 11
<212> TYPE: PRT
<213> ORGANISM: Artificial Sequence
<220> FEATURE:
<223> OTHER INFORMATION: Synthetic peptide

<400> SEQUENCE: 9

Tyr Ala Arg Ala Ala Ala Arg Gln Ala Arg Ala
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Synthetic peptide
```

```
<400> SEQUENCE: 10

Arg Arg Arg Arg Arg Arg Arg Arg
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic peptide

<400> SEQUENCE: 11

Lys Lys Lys Lys Lys Lys Lys Lys
1               5

<210> SEQ ID NO 12
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (25)..(25)
<223> OTHER INFORMATION: Xaa can be any naturally occurring amino acid

<400> SEQUENCE: 12

Gly Trp Thr Leu Asn Ser Ala Gly Tyr Leu Leu Gly Lys Ile Asn Leu
1               5                   10                  15

Lys Ala Leu Ala Ala Leu Ala Lys Xaa Ile Leu
            20                  25

<210> SEQ ID NO 13
<211> LENGTH: 18
<212> TYPE: PRT
<213> ORGANISM: Artificial Sequence
<220> FEATURE:
<223> OTHER INFORMATION: Synthetic peptide

<400> SEQUENCE: 13

Leu Leu Ile Leu Leu Arg Arg Arg Ile Arg Lys Gln Ala Asn Ala His
1               5                   10                  15

Ser Lys

<210> SEQ ID NO 14
<211> LENGTH: 16
<212> TYPE: PRT
<213> ORGANISM: Artificial Sequence
<220> FEATURE:
<223> OTHER INFORMATION: Synthetic peptide

<400> SEQUENCE: 14

Ser Arg Arg His His Cys Arg Ser Lys Ala Lys Arg Ser Arg His His
1               5                   10                  15

<210> SEQ ID NO 15
<211> LENGTH: 11
<212> TYPE: PRT
<213> ORGANISM: Artificial Sequence
<220> FEATURE:
<223> OTHER INFORMATION: Synthetic peptide

<400> SEQUENCE: 15

Asn Arg Ala Arg Arg Asn Arg Arg Arg Val Arg
1               5                   10
```

<210> SEQ ID NO 16
<211> LENGTH: 15
<212> TYPE: PRT
<213> ORGANISM: Artificial Sequence
<220> FEATURE:
<223> OTHER INFORMATION: Synthetic peptide

<400> SEQUENCE: 16

Arg Gln Leu Arg Ile Ala Gly Arg Arg Leu Arg Gly Arg Ser Arg
1               5                   10                  15

<210> SEQ ID NO 17
<211> LENGTH: 13
<212> TYPE: PRT
<213> ORGANISM: Artificial Sequence
<220> FEATURE:
<223> OTHER INFORMATION: Synthetic peptide

<400> SEQUENCE: 17

Lys Leu Ile Lys Gly Arg Thr Pro Ile Lys Phe Gly Lys
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic peptide

<400> SEQUENCE: 18

Arg Arg Ile Pro Asn Arg Arg Pro Arg Arg
1               5                   10

<210> SEQ ID NO 19
<211> LENGTH: 18
<212> TYPE: PRT
<213> ORGANISM: Artificial Sequence
<220> FEATURE:
<223> OTHER INFORMATION: Synthetic peptide

<400> SEQUENCE: 19

Lys Leu Ala Leu Lys Leu Ala Leu Lys Ala Leu Lys Ala Ala Leu Lys
1               5                   10                  15

Leu Ala

<210> SEQ ID NO 20
<211> LENGTH: 14
<212> TYPE: PRT
<213> ORGANISM: Artificial Sequence
<220> FEATURE:
<223> OTHER INFORMATION: Synthetic peptide

<400> SEQUENCE: 20

Lys Leu Ala Lys Leu Ala Lys Lys Leu Ala Lys Leu Ala Lys
1               5                   10

<210> SEQ ID NO 21
<211> LENGTH: 27
<212> TYPE: PRT
<213> ORGANISM: Artificial Sequence
<220> FEATURE:
<223> OTHER INFORMATION: Synthetic peptide

<400> SEQUENCE: 21

Gly Ala Leu Phe Leu Gly Phe Leu Gly Ala Ala Gly Ser Thr Asn Gly

```
                1               5                   10                  15
Ala Trp Ser Gln Pro Lys Lys Arg Lys Val
            20                  25

<210> SEQ ID NO 22
<211> LENGTH: 21
<212> TYPE: PRT
<213> ORGANISM: Artificial Sequence
<220> FEATURE:
<223> OTHER INFORMATION: Synthetic peptide

<400> SEQUENCE: 22

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 23
<211> LENGTH: 23
<212> TYPE: PRT
<213> ORGANISM: Artificial Sequence
<220> FEATURE:
<223> OTHER INFORMATION: Synthetic peptide

<400> SEQUENCE: 23

Gly Ala Leu Phe Leu Gly Trp Leu Gly Ala Ala Gly Ser Thr Met Gly
1               5                   10                  15

Ala Lys Lys Lys Arg Lys Val
            20

<210> SEQ ID NO 24
<211> LENGTH: 23
<212> TYPE: PRT
<213> ORGANISM: Artificial Sequence
<220> FEATURE:
<223> OTHER INFORMATION: Synthetic peptide

<400> SEQUENCE: 24

Met Gly Leu Gly Leu His Leu Leu Val Leu Ala Ala Ala Leu Gln Gly
1               5                   10                  15

Ala Lys Ser Lys Arg Lys Val
            20

<210> SEQ ID NO 25
<211> LENGTH: 26
<212> TYPE: PRT
<213> ORGANISM: Artificial Sequence
<220> FEATURE:
<223> OTHER INFORMATION: Synthetic peptide

<400> SEQUENCE: 25

Ala Ala Val Ala Leu Leu Pro Ala Val Leu Leu Ala Leu Leu Ala Pro
1               5                   10                  15

Ala Ala Ala Asn Tyr Lys Lys Pro Lys Leu
            20                  25

<210> SEQ ID NO 26
<211> LENGTH: 28
<212> TYPE: PRT
<213> ORGANISM: Artificial Sequence
<220> FEATURE:
<223> OTHER INFORMATION: Synthetic peptide

<400> SEQUENCE: 26
```

```
Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25
```

<210> SEQ ID NO 27
<211> LENGTH: 24
<212> TYPE: PRT
<213> ORGANISM: Artificial Sequence
<220> FEATURE:
<223> OTHER INFORMATION: Synthetic peptide

<400> SEQUENCE: 27

```
Leu Gly Thr Tyr Thr Gln Asp Phe Asn Lys Phe His Thr Phe Pro Gln
1               5                   10                  15

Thr Ala Ile Gly Val Gly Ala Pro
            20
```

<210> SEQ ID NO 28
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (24)..(24)
<223> OTHER INFORMATION: Xaa can be any naturally occurring amino acid

<400> SEQUENCE: 28

```
Asp Pro Lys Gly Asp Pro Lys Gly Val Thr Val Thr Val Thr Val Thr
1               5                   10                  15

Val Thr Gly Lys Gly Asp Pro Xaa Pro Asp
            20                  25
```

<210> SEQ ID NO 29
<211> LENGTH: 14
<212> TYPE: PRT
<213> ORGANISM: Artificial Sequence
<220> FEATURE:
<223> OTHER INFORMATION: Synthetic peptide

<400> SEQUENCE: 29

```
Pro Pro Pro Pro Pro Pro Pro Pro Pro Pro Pro Pro Pro Pro
1               5                   10
```

<210> SEQ ID NO 30
<211> LENGTH: 18
<212> TYPE: PRT
<213> ORGANISM: Artificial Sequence
<220> FEATURE:
<223> OTHER INFORMATION: Synthetic peptide

<400> SEQUENCE: 30

```
Val Arg Leu Pro Pro Pro Val Arg Leu Pro Pro Pro Val Arg Leu Pro
1               5                   10                  15

Pro Pro
```

<210> SEQ ID NO 31
<211> LENGTH: 10
<212> TYPE: PRT
<213> ORGANISM: Artificial Sequence
<220> FEATURE:
<223> OTHER INFORMATION: Synthetic peptide

<400> SEQUENCE: 31

```
Pro Arg Pro Leu Pro Pro Pro Arg Pro Gly
1               5                   10
```

<210> SEQ ID NO 32
<211> LENGTH: 30
<212> TYPE: PRT
<213> ORGANISM: Artificial Sequence
<220> FEATURE:
<223> OTHER INFORMATION: Synthetic peptide

<400> SEQUENCE: 32

```
Ser Val Arg Arg Arg Pro Arg Pro Pro Tyr Leu Pro Arg Pro Arg Pro
1               5                   10                  15

Pro Pro Phe Phe Pro Pro Arg Leu Pro Pro Arg Ile Pro Pro
            20                  25                  30
```

<210> SEQ ID NO 33
<211> LENGTH: 21
<212> TYPE: PRT
<213> ORGANISM: Artificial Sequence
<220> FEATURE:
<223> OTHER INFORMATION: Synthetic peptide

<400> SEQUENCE: 33

```
Thr Arg Ser Ser Arg Ala Gly Leu Gln Phe Pro Val Gly Arg Val His
1               5                   10                  15

Arg Leu Leu Arg Lys
            20
```

<210> SEQ ID NO 34
<211> LENGTH: 23
<212> TYPE: PRT
<213> ORGANISM: Artificial Sequence
<220> FEATURE:
<223> OTHER INFORMATION: Synthetic peptide

<400> SEQUENCE: 34

```
Gly Ile Gly Lys Phe Leu His Ser Ala Lys Lys Phe Gly Lys Ala Phe
1               5                   10                  15

Val Gly Glu Ile Met Asn Ser
            20
```

<210> SEQ ID NO 35
<211> LENGTH: 37
<212> TYPE: PRT
<213> ORGANISM: Artificial Sequence
<220> FEATURE:
<223> OTHER INFORMATION: Synthetic peptide

<400> SEQUENCE: 35

```
Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
            20                  25                  30

Thr Gln Ile Ala Lys
            35
```

<210> SEQ ID NO 36
<211> LENGTH: 28
<212> TYPE: PRT
<213> ORGANISM: Artificial Sequence
<220> FEATURE:
<223> OTHER INFORMATION: Synthetic peptide

```
<400> SEQUENCE: 36

Ala Leu Trp Met Thr Leu Leu Lys Lys Val Leu Lys Ala Ala Ala Lys
1               5                   10                  15

Ala Ala Leu Asn Ala Val Leu Val Gly Ala Asn Ala
                20                  25

<210> SEQ ID NO 37
<211> LENGTH: 26
<212> TYPE: PRT
<213> ORGANISM: Artificial Sequence
<220> FEATURE:
<223> OTHER INFORMATION: Synthetic peptide

<400> SEQUENCE: 37

Gly Ile Gly Ala Val Leu Lys Val Leu Thr Thr Gly Leu Pro Ala Leu
1               5                   10                  15

Ile Ser Trp Ile Lys Arg Lys Arg Gln Gln
                20                  25

<210> SEQ ID NO 38
<211> LENGTH: 14
<212> TYPE: PRT
<213> ORGANISM: Artificial Sequence
<220> FEATURE:
<223> OTHER INFORMATION: Synthetic peptide

<400> SEQUENCE: 38

Ile Asn Leu Lys Ala Leu Ala Ala Leu Ala Lys Lys Ile Leu
1               5                   10

<210> SEQ ID NO 39
<211> LENGTH: 33
<212> TYPE: PRT
<213> ORGANISM: Artificial Sequence
<220> FEATURE:
<223> OTHER INFORMATION: Synthetic peptide

<400> SEQUENCE: 39

Gly Phe Phe Ala Leu Ile Pro Lys Ile Ile Ser Ser Pro Leu Pro Lys
1               5                   10                  15

Thr Leu Leu Ser Ala Val Gly Ser Ala Leu Gly Gly Ser Gly Gly Gln
                20                  25                  30

Glu

<210> SEQ ID NO 40
<211> LENGTH: 15
<212> TYPE: PRT
<213> ORGANISM: Artificial Sequence
<220> FEATURE:
<223> OTHER INFORMATION: Synthetic peptide

<400> SEQUENCE: 40

Leu Ala Lys Trp Ala Leu Lys Gln Gly Phe Ala Lys Leu Lys Ser
1               5                   10                  15

<210> SEQ ID NO 41
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(23)
<223> OTHER INFORMATION: Xaa can be any naturally occurring amino acid
```

```
<400> SEQUENCE: 41

Ser Met Ala Gln Asp Ile Ile Ser Thr Ile Gly Asp Leu Val Lys Trp
1               5                   10                  15

Ile Ile Gln Thr Val Asn Xaa Phe Thr Lys Lys
            20                  25

<210> SEQ ID NO 42
<211> LENGTH: 41
<212> TYPE: PRT
<213> ORGANISM: Artificial Sequence
<220> FEATURE:
<223> OTHER INFORMATION: Synthetic peptide

<400> SEQUENCE: 42

Leu Leu Gly Asp Phe Phe Arg Lys Ser Lys Glu Lys Ile Gly Lys Glu
1               5                   10                  15

Phe Lys Arg Ile Val Gln Arg Ile Lys Gln Arg Ile Lys Asp Phe Leu
            20                  25                  30

Ala Asn Leu Val Pro Arg Thr Glu Ser
        35                  40

<210> SEQ ID NO 43
<211> LENGTH: 20
<212> TYPE: PRT
<213> ORGANISM: Artificial Sequence
<220> FEATURE:
<223> OTHER INFORMATION: Synthetic peptide

<400> SEQUENCE: 43

Leu Lys Lys Leu Leu Lys Lys Leu Leu Lys Lys Leu Leu Lys Lys Leu
1               5                   10                  15

Leu Lys Lys Leu
            20

<210> SEQ ID NO 44
<211> LENGTH: 18
<212> TYPE: PRT
<213> ORGANISM: Artificial Sequence
<220> FEATURE:
<223> OTHER INFORMATION: Synthetic peptide

<400> SEQUENCE: 44

Lys Leu Lys Leu Lys Leu Lys Leu Lys Leu Lys Leu Lys Leu Lys Leu
1               5                   10                  15

Lys Leu

<210> SEQ ID NO 45
<211> LENGTH: 18
<212> TYPE: PRT
<213> ORGANISM: Artificial Sequence
<220> FEATURE:
<223> OTHER INFORMATION: Synthetic peptide

<400> SEQUENCE: 45

Pro Ala Trp Arg Lys Ala Phe Arg Trp Ala Trp Arg Met Leu Lys Lys
1               5                   10                  15

Ala Ala

<210> SEQ ID NO 46
<211> LENGTH: 18
<212> TYPE: PRT
<213> ORGANISM: Artificial Sequence
```

```
<220> FEATURE:
<223> OTHER INFORMATION: Synthetic peptide

<400> SEQUENCE: 46

Phe Ser Ser Leu Leu Lys Lys Arg Asp Ser Phe Arg Arg Asp Ser Lys
1               5                   10                  15

Leu Glu

<210> SEQ ID NO 47
<211> LENGTH: 18
<212> TYPE: PRT
<213> ORGANISM: Artificial Sequence
<220> FEATURE:
<223> OTHER INFORMATION: Synthetic peptide

<400> SEQUENCE: 47

Phe Ser Ser Leu Leu Lys Lys Arg Asp Ala Phe Arg Arg Asp Ala Lys
1               5                   10                  15

Leu Glu

<210> SEQ ID NO 48
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X is A, V or D

<400> SEQUENCE: 48

Phe Ser Ser Leu Leu Lys Lys Arg Asp Xaa Phe Arg Arg Asp
1               5                   10

<210> SEQ ID NO 49
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X is A, V or D
<220> FEATURE:
<221> NAME/KEY: MISC_FEATURE
<222> LOCATION: (15)..(15)
<223> OTHER INFORMATION: X is A, V or D

<400> SEQUENCE: 49

Phe Ser Ser Leu Leu Lys Lys Arg Asp Xaa Phe Arg Arg Asp Xaa Lys
1               5                   10                  15

<210> SEQ ID NO 50
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X is A, V or D
<220> FEATURE:
<221> NAME/KEY: MISC_FEATURE
<222> LOCATION: (11)..(11)
<223> OTHER INFORMATION: X is A, V or D
```

-continued

<400> SEQUENCE: 50

Leu Lys Lys Arg Asp Xaa Phe Arg Arg Asp Xaa Lys Leu Glu
1               5                   10

<210> SEQ ID NO 51
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: X is A, V or D
<220> FEATURE:
<221> NAME/KEY: MISC_FEATURE
<222> LOCATION: (13)..(13)
<223> OTHER INFORMATION: X is A, V or D

<400> SEQUENCE: 51

Ser Leu Leu Lys Lys Arg Asp Xaa Phe Arg Arg Asp Xaa Lys Leu Glu
1               5                   10                  15

<210> SEQ ID NO 52
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: X is A, V or D
<220> FEATURE:
<221> NAME/KEY: MISC_FEATURE
<222> LOCATION: (15)..(15)
<223> OTHER INFORMATION: X is A, V or D

<400> SEQUENCE: 52

Phe Ser Ser Leu Leu Lys Lys Arg Asp Xaa Phe Arg Arg Asp Xaa Lys
1               5                   10                  15

Leu Glu

<210> SEQ ID NO 53
<211> LENGTH: 16
<212> TYPE: PRT
<213> ORGANISM: Artificial Sequence
<220> FEATURE:
<223> OTHER INFORMATION: Synthetic peptide

<400> SEQUENCE: 53

Ser Leu Leu Lys Lys Arg Asp Ala Phe Arg Arg Asp Ala Lys Leu Glu
1               5                   10                  15

<210> SEQ ID NO 54
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X is A, V or D
<220> FEATURE:
<221> NAME/KEY: MISC_FEATURE
<222> LOCATION: (15)..(15)
<223> OTHER INFORMATION: X is A, V or D

<400> SEQUENCE: 54

Phe Ser Ser Leu Leu Lys Lys Arg Xaa Ala Phe Arg Arg Asp Xaa Lys
1               5                   10                  15

Leu Glu

<210> SEQ ID NO 55
<211> LENGTH: 14
<212> TYPE: PRT
<213> ORGANISM: Artificial Sequence
<220> FEATURE:
<223> OTHER INFORMATION: Synthetic peptide

<400> SEQUENCE: 55

Leu Lys Lys Arg Asp Ala Phe Arg Arg Asp Ala Lys Leu Glu
1               5                   10

<210> SEQ ID NO 56
<211> LENGTH: 16
<212> TYPE: PRT
<213> ORGANISM: Artificial Sequence
<220> FEATURE:
<223> OTHER INFORMATION: Synthetic peptide

<400> SEQUENCE: 56

Phe Ser Ser Leu Leu Lys Lys Arg Asp Ala Phe Arg Arg Asp Ala Lys
1               5                   10                  15

<210> SEQ ID NO 57
<211> LENGTH: 14
<212> TYPE: PRT
<213> ORGANISM: Artificial Sequence
<220> FEATURE:
<223> OTHER INFORMATION: Synthetic peptide

<400> SEQUENCE: 57

Phe Ser Ser Leu Leu Lys Lys Arg Asp Ala Phe Arg Arg Asp
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Synthetic peptide

<400> SEQUENCE: 58

Leu Lys Lys Arg Asp Ala Phe Arg Arg Asp
1               5                   10

<210> SEQ ID NO 59
<211> LENGTH: 18
<212> TYPE: PRT
<213> ORGANISM: Artificial Sequence
<220> FEATURE:
<223> OTHER INFORMATION: Synthetic peptide

<400> SEQUENCE: 59

Asp Ala Leu Phe Lys Lys Ala Lys Ser Leu Arg Phe Glu Leu Arg Ser
1               5                   10                  15

Arg Asp

INHIBITION OF MYBP-C BINDING TO MYOSIN AS A TREATMENT FOR HEART FAILURE

This application claims benefit of priority to U.S. Provisional Application 61/663,200, filed Jun. 22, 2012, the entire contents of which are hereby incorporated by reference.

This invention was made with government support under HL082900 awarded by the National Institutes of Health. The government has certain rights in the invention.

BACKGROUND OF THE INVENTION

1. Field of the Invention

The present invention relates generally to the fields of biology and medicine. More particularly, it concerns molecular interactions between Myosin Binding Protein C (MyBP-C) and myosin in cardiac muscle. Specifically, the invention relates to the use of inhibitors of the interaction between MyBP-C and myosin to increase the force of cardiac muscle contraction and the rate of pressure development in the heart.

2. Description of Related Art

Heart failure is one of the leading causes of morbidity and mortality in the world. In the U.S. alone, estimates indicate that 3 million people are currently living with cardiomyopathy and another 400,000 are diagnosed on a yearly basis. Dilated cardiomyopathy (DCM), also referred to as "congestive cardiomyopathy," is the most common form of the cardiomyopathies and has an estimated prevalence of nearly 40 per 100,000 individuals (Durand et al., 1995). Approximately half of DCM cases are idiopathic, and of these, familial dilated cardiomyopathy has been indicated as representing approximately 20%. The remaining half of DCM cases are associated with known disease processes, such as untreated hypertension or valvular heart disease, as an end-stage condition. Furthermore, serious myocardial damage can result from certain drugs used in cancer chemotherapy (e.g., doxorubicin and daunoribucin). In addition, many DCM patients are chronic alcoholics. Fortunately, for these patients, the progression of myocardial dysfunction may be stopped or reversed if alcohol consumption is reduced or stopped early in the course of disease. Peripartum cardiomyopathy is another idiopathic form of DCM, as is disease associated with infectious sequelae. In sum, cardiomyopathies, including inherited or acquired DCM, are significant public health problems.

Heart disease and its manifestations, including coronary artery disease, myocardial infarction, congestive heart failure and cardiac hypertrophy, clearly present a major health risk in the United States today. The cost to diagnose, treat and support patients suffering from these diseases is well into the billions of dollars. Two particularly severe manifestations of heart disease are myocardial infarction and cardiac hypertrophy. With respect to myocardial infarction, typically an acute thrombocytic coronary occlusion occurs in a coronary artery as a result of atherosclerosis and causes myocardial cell death. Because cardiomyocytes, the heart muscle cells, are terminally differentiated and generally incapable of cell division, they are typically replaced by scar tissue when they die during the course of an acute myocardial infarction. Scar tissue is not contractile, fails to contribute to cardiac function, and often plays a detrimental role in heart function by expanding during cardiac contraction, or by increasing the size and effective radius of the ventricle, for example, becoming hypertrophic. With respect to non-physiological (i.e., not due to exercise training) cardiac hypertrophy, one theory regards this as a disease that resembles aberrant development and, as such, raises the question of whether developmental signals in the heart can contribute to hypertrophic disease. Cardiac hypertrophy is an adaptive response of the heart to virtually all forms of cardiac disease, including those arising from hypertension, mechanical load, myocardial infarction, cardiac arrhythmias, endocrine disorders, and genetic mutations in cardiac contractile protein genes. While the hypertrophic response is initially a compensatory mechanism that augments cardiac output, sustained hypertrophy can lead to DCM, heart failure, and sudden death. In the United States, approximately half a million individuals are diagnosed with heart failure each year, with a five-year mortality rate approaching 50%.

The causes and effects of cardiac hypertrophy have been extensively documented, but the underlying molecular mechanisms have not been elucidated. Understanding these mechanisms is a major concern in the prevention and treatment of cardiac disease and will be crucial as a therapeutic modality in designing new drugs that specifically target cardiac hypertrophy and subsequent heart failure. As pathologic cardiac hypertrophy most often does not produce any symptoms until the cardiac damage is severe enough to produce heart failure, the symptoms of cardiomyopathy are those associated with heart failure. These symptoms include shortness of breath, fatigue with exertion, the inability to lie flat without becoming short of breath (orthopnea), paroxysmal nocturnal dyspnea, enlarged cardiac dimensions, and/or swelling in the lower legs. Patients also often present with increased blood pressure, extra heart sounds, cardiac murmurs, pulmonary and systemic emboli, chest pain, pulmonary congestion, and palpitations. In addition, DCM causes decreased ejection fractions (i.e., a measure of both intrinsic systolic function and remodeling). The disease is further characterized by ventricular dilation and grossly impaired systolic function due to diminished myocardial contractility, which results in dilated heart failure in many patients. Affected hearts also undergo cell/chamber remodeling as a result of the myocyte/myocardial dysfunction, which contributes to the "DCM phenotype." As the disease progresses so do the symptoms. Patients with DCM also have a greatly increased incidence of life-threatening arrhythmias, including ventricular tachycardia and ventricular fibrillation. In these patients, an episode of syncope (dizziness) is regarded as a harbinger of sudden death.

Diagnosis of dilated cardiomyopathy typically depends upon the demonstration of enlarged heart chambers, particularly enlarged ventricles. Enlargement is commonly observable on chest X-rays, but is more accurately assessed using echocardiograms. DCM is often difficult to distinguish from acute myocarditis, valvular heart disease, coronary artery disease, and hypertensive heart disease. Once the diagnosis of dilated cardiomyopathy is made, every effort is made to identify and treat potentially reversible causes and prevent further heart damage. For example, coronary artery disease and valvular heart disease must be ruled out. Anemia, abnormal tachycardias, nutritional deficiencies, alcoholism, thyroid disease and/or other problems need to be addressed and controlled.

As mentioned above, treatment with pharmacological agents still represents the primary mechanism for reducing or eliminating the manifestations of heart failure. Diuretics constitute the first line of treatment for mild-to-moderate heart failure by reducing the volume load on the heart. Unfortunately, many of the commonly used diuretics (e.g., the thiazides) have numerous adverse effects. For example, certain diuretics may increase serum cholesterol and triglycerides. Moreover, diuretics are generally ineffective for patients suffering from severe heart failure. If diuretics are ineffective, vasodilatory agents may be used. The angiotensin converting (ACE) inhibitors (e.g., enalopril and lisinopril) not only provide symptomatic relief, they also have been reported to decrease mortality (Young et al., 1989). Again, however, the ACE inhibitors are associated with adverse effects that result in their being contraindicated in patients with certain disease states (e.g., renal artery stenosis). Similarly, inotropic agent therapy (i.e., a drug that improves cardiac output by increasing the force of myocardial muscle contraction) is associated with a panoply of adverse reactions, including gastrointestinal problems and central nervous system dysfunction. Thus, the currently used pharmacological agents have severe shortcomings in particular patient populations. The availability of new, safe and effective agents would undoubtedly benefit patients who either cannot use the pharmacological modalities presently available, or who do not receive adequate relief from those modalities.

SUMMARY OF THE INVENTION

Thus, in accordance with the present invention, there is provided a method of treating heart failure comprising (a) identifying a patient exhibiting one or more symptoms of heart failure; and (b) administering to said patient an inhibitor of the interaction of Myosin Binding Protein C (MyBP-C) with myosin. The inhibitor may be a peptide derived from the MyBP-C binding site for myosin. Such a peptide may be of no more than 50 residues and comprise the sequence LKKRDXFRRD (SEQ ID NO: 1), where X is A, V or D. The peptide may also comprise, consist essentially of or consist of the sequence FSSLLKKRDXFRRD (SEQ ID NO: 48), FSSLLKKRDXFRRDXK (SEQ ID NO: 49), LKKRDXFRRDXKLE (SEQ ID NO: 50), SLLKKRDXFRRDXKLE (SEQ ID NO: 51), or FSSLLKKRDXFRRDXKLE (SEQ ID NO: 52), and optionally may be no more than 25, 30, 35, 40 or 45 residues. The peptide may comprise a cell penetrating domain. The peptide may comprise some or all D-amino acids, such as an all D-amino acid peptide in a retro-inverso configuration.

Administering the inhibitor may be performed intramuscularly, intravenously or by direct injection into cardiac tissue, or may comprise oral, transdermal, sustained release, controlled release, delayed release, suppository, or sublingual administration. The method may further comprise administering to said patient a second heart failure therapy. The second therapy may be selected from the group consisting of a beta blocker, an ionotrope, a diuretic, ACE-I, AII antagonist, BNP, or a Ca$^{++}$ channel blocker. The second therapy may be administered at the same time as said inhibitor of the interaction of MyBP-C and myosin or either before or after said inhibitor of the interaction of MyBP-C and myosin.

Treating may comprise improving one or more symptoms of heart failure, such as increased exercise capacity, increased cardiac ejection volume, increased cardiac ejection fraction, decreased left ventricular end diastolic pressure, decreased pulmonary capillary wedge pressure, increased cardiac output, or cardiac index, lowered pulmonary artery pressures, decreased left ventricular end systolic and diastolic dimensions, decreased left and right ventricular wall stress, decreased wall tension, increased quality of life, and decreased disease-related morbidity or mortality.

In another embodiment, there is provided a method of slowing the progression of heart failure comprising (a) identifying a patient at risk of developing severe heart failure; and (b) administering to said patient an inhibitor of the interaction of Myosin Binding Protein C (MyBP-C) and myosin. The inhibitor may be a peptide derived from the MyBP-C binding site for myosin. Such a peptide may be of no more than 50 residues and comprise the sequence LKKRDXFRRD (SEQ ID NO: 1), where X is A, V or D. The peptide may also comprise, consist essentially of or consist of the sequence FSSLLKKRDXFRRD (SEQ ID NO: 48), FSSLLKKRDXFRRDXK (SEQ ID NO: 49), LKKRDXFRRDXKLE (SEQ ID NO: 50), SLLKKRDXFRRDXKLE (SEQ ID NO: 51), or FSSLLKKRDXFRRDXKLE (SEQ ID NO: 52), and optionally may be no more than 25, 30, 35, 40 or 45 residues. The peptide may comprise a cell penetrating domain. The peptide may comprise some or all D-amino acids, such as an all D-amino acid peptide in a retro-inverso configuration.

Administering may be performed intramuscularly, intravenously or by direct injection into cardiac tissue, or may comprise oral, transdermal, sustained release, controlled release, delayed release, suppository, or sublingual administration. The patient at risk may exhibit one or more of a list of risk factors comprising long-standing uncontrolled hypertension, uncorrected valvular disease, chronic angina, recent myocardial infarction, congenital predisposition to heart disease or pathological hypertrophy. The patient at risk may be diagnosed as having a genetic predisposition to heart failure, and/or have a familial history of heart failure. The method may further comprise administering to said patient a second heart failure therapy, such as a beta blocker, an ionotrope, a diuretic, ACE-I, AII antagonist, BNP, or a Ca$^{++}$ channel blocker. The subject may be a heart transplant recipient.

In other embodiments, there are provided:

a method of increasing exercise tolerance in a subject with heart failure comprising administering to said subject an inhibitor of the interaction of Myosin Binding Protein C (MyBP-C) and myosin;

a method of reducing hospitalization in a subject with heart failure comprising administering to said subject an inhibitor of the interaction of Myosin Binding Protein C (MyBP-C) and myosin;

a method of improving quality of life in a subject with heart failure comprising administering to said subject an inhibitor of the interaction of Myosin Binding Protein C (MyBP-C) and myosin;

a method of decreasing morbidity in a subject with heart failure comprising administering to said subject an inhibitor of the interaction of Myosin Binding Protein C (MyBP-C) and myosin; or a method of decreasing mortality in a subject with heart failure comprising administering to said patient an inhibitor of the interaction of Myosin Binding Protein C (MyBP-C) and myosin.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF ILLUSTRATIVE EMBODIMENTS

Figure 1:
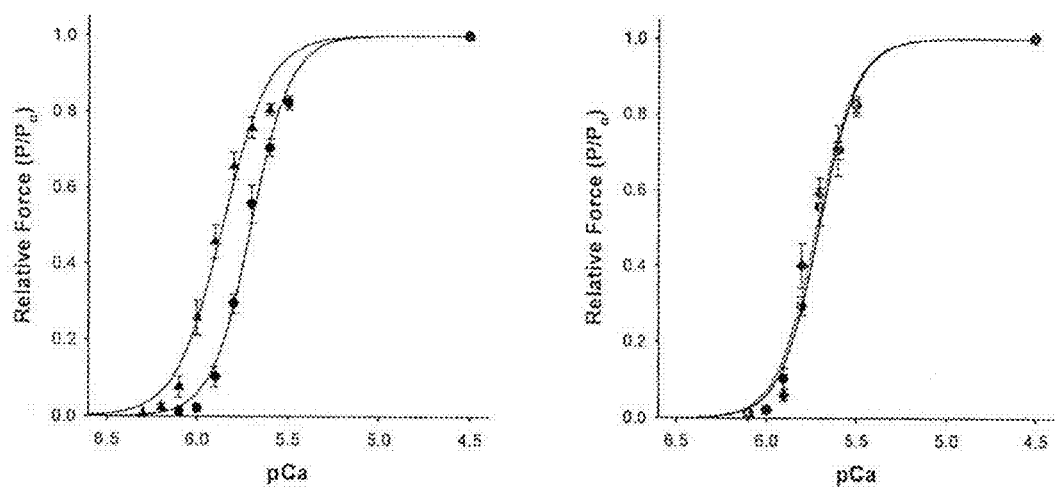
FIG. 1. Force pCa relationships obtained in absence or presence of peptide. Left panel: The force-pCa relationship was shifted to lower $Ca^{2+}$ concentrations by infusion of the 302a peptide. Circles are control data before peptide; triangles are experimental data following peptide treatment. Right panel: The force-pCa relationship was unaffected by treatment with a scrambled peptide. Circles are control data before peptide; diamonds are experimental data following peptide treatment.

Heart failure is generally characterized as an inability of the heart to pump adequate amounts of blood throughout the body. Heart attacks, heart disease, and hypertension can all lead to heart failure. It is estimated that 2% of adults in developed countries suffer from heart failure and that number increases to 6-10% of people over the age of 65. To overcome the symptoms of heart failure, pharmaceuticals that improve the force and number of heart contractions are needed. The present invention provides a novel approach to achieving increased force and power of cardiac muscle contractions using new therapeutic compositions. These are discussed in detail below.

I. MYOSIN

Myosins comprise a family of ATP-dependent motor proteins and are best known for their role in muscle contraction and their involvement in a wide range of other eukaryotic motility processes. They are responsible for actin-based motility. The term was originally used to describe a group of similar ATPases found in striated and smooth muscle cells. Thus, although myosin was originally thought to be restricted to muscle cells, there is no single "myosin" but rather a huge superfamily of genes whose protein products share the basic properties of actin binding, ATP hydrolysis (ATPase enzyme activity), and force transduction. Virtually all eukaryotic cells contain myosin isoforms. Some isoforms have specialized functions in certain cell types (such as muscle), while other isoforms are ubiquitous. The structure and function of myosin is strongly conserved across species, to the extent that rabbit muscle myosin II will bind to actin from an amoeba.

Most myosin molecules are composed of a head, neck, and tail domain. The head domain binds the filamentous actin, and uses ATP hydrolysis to generate force and to "walk" along the filament towards the barbed (+) end (with the exception of myosin VI, which moves towards the pointed (−) end). The neck domain acts as a linker and as a lever arm for transducing force generated by the catalytic motor domain. The neck domain can also serve as a binding site for myosin light chains which are distinct proteins that form part of a macromolecular complex and generally have regulatory functions. The tail domain generally mediates interaction with cargo molecules and/or other myosin subunits. In some cases, the tail domain may play a role in regulating motor activity.

Multiple myosin II molecules generate force in skeletal muscle through a power stroke mechanism fuelled by the energy released from ATP hydrolysis. The power stroke occurs at the release of phosphate from the myosin molecule after the ATP hydrolysis while myosin is tightly bound to actin. The effect of this release is a conformational change in the molecule that pulls against the actin. The release of the ADP molecule and binding of a new ATP molecule will release myosin from actin. ATP hydrolysis within the myosin will cause it to bind to actin again to repeat the cycle. The combined effect of the myriad power strokes causes the muscle to contract.

Myosin II (also known as conventional myosin) is the myosin type responsible for producing muscle contraction in muscle cells. Myosin II contains two heavy chains, each about 2000 amino acids in length, which constitute the head and tail domains. Each of these heavy chains contains the N-terminal head domain, while the C-terminal tails take on a coiled-coil morphology, holding the two heavy chains together (imagine two snakes wrapped around each other, such as in a caduceus). Thus, myosin II has two heads. The intermediate neck domain is the region creating the angle between the head and tail. In smooth muscle, a single gene (MYH11) codes for the heavy chains myosin II, but splice variants of this gene result in four distinct isoforms. It also contains 4 light chains, resulting in 2 per head, weighing 20 (MLC20) and 17 (MLC17) kDa. These bind the heavy chains in the "neck" region between the head and tail. The MLC20 is also known as the regulatory light chain and actively participates in muscle contraction. The MLC17 is also known as the essential light chain. Its exact function is unclear, but is believed to contribute to the structural stability of the myosin, head along with MLC20. Two variants of MLC17 (MLC17a/b) exist as a result of alternate splicing at the MLC17 gene.

In muscle cells, the long coiled-coil tails of the individual myosin molecules join together, forming the thick filaments of the sarcomere. The force-producing head domains stick out from the side of the thick filament, ready to walk along the adjacent actin-based thin filaments in response to the proper chemical signals.

II. MYOSIN BINDING PROTEIN C

Myosin binding protein C (MyBP-C) has been shown by this laboratory to be a central regulator of the kinetics of cardiac contraction. In murine models, the inventors have observed in published work that genetic ablation or phosphorylation of MyBP-C by PKA or CAMKII accelerates the kinetics of contraction and increases the force of contraction in cardiac muscle. Most recently, the inventors have shown in unpublished work that CAMKII phosphorylation of MyBP-C at residues S282 and S302 in the mouse and S284 and S304 in the human underlies the increase in myocardial force of contraction as heart rate is increased, the so-called staircase phenomenon. Proof for this conclusion was obtained by observing that (1) phosphorylation at these two residues is increased when stimulus frequency is increased, but other potential phosphorylation sites are not, and (2) the staircase phenomenon is absent in hearts in which these residues are replaced with non-phosphorylatable residues. In terms of molecular mechanism, the inventors believe that MyBP-C normally depresses the speed and strength of contraction by means of its interaction with the contractile protein myosin and thereby reduces the probability of myosin binding to actin. Ablation of MyBP-C or phosphorylation of MyBP-C by PKA or CAMKII disrupts this interaction (we have evidence for this for PKA from the inventors published in vitro studies) and relieves the repression of myosin by MyBP-C (the inventors have evidence for this from their published x-ray diffraction studies). Once phosphorylated, MyBP-C no longer binds to myosin, myosin moves closer to actin, the probability of myosin binding to actin increases, and the speed and strength of contraction both increase.

In heart failure, MyBP-C is phosphorylated minimally or not at all by either PKA or CAMKII due to down-regulation of β-adrenergic receptors. Based on the inventors' findings that phosphorylation of MyBP-C improves contraction, the inventors propose to target the CAMKII site(s) on MyBP-C with a small-molecule pharmaceutical to disrupt its interaction with myosin and thereby improve cardiac contraction and pump function. This approach is far superior to targeting PKA sites since there are many fewer CAMKII phosphorylation sites in the heart, which improves specificity of targeting. By specifically targeting residues S282 and/or S302 in the mouse and S284 and/or S304 in the human, it should be possible to minimize any increase in metabolic load on the heart that might be introduced by increased strength of beating, an increase that would not be tolerated well by a failing heart.

III. PEPTIDE INHIBITORS

A. Structure

The present invention contemplates the design, production and use of various MyBP-C peptides. The structural features of these peptides are as follows. First, the peptides will generally have no more than 50 consecutive residues of a MyBP-C. Thus, the term "a peptide having no more than 50 consecutive residues," even when including the term "comprising," cannot be understood to comprise a greater number of consecutive MyBP-C residues. Second, the peptides will contain the motifs responsible for interaction with myosin. In general, the peptides will have, at a minimum, 8 consecutive residues of the MyBP-C.

In general, the peptides will be 15-50 residues or less, again, comprising no more than 50 consecutive residues of a MyBP-C. The overall length may be 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 residues. Ranges of peptide length of 10-50 residues, 15-50 residues, 20-25 residues, 25-50 residues, 30-50 residues, 35-50, residues, 10-20 residues, 15-20 residues, 15-25 residues, 15-30 residues, 20-25 residues, and 20-25 residues are contemplated. The number of consecutive MyBP-C residues may be 8, 9, 10, 11, 12, 13, 14, 15, 16, 17, 18, 19, 20 or greater. Ranges of consecutive residues of 15-20 residues, 20-25 residues, 15-30, residues, 20-30 residues or 15-25 residues are contemplated.

The present invention may utilize L-configuration amino acids, D-configuration amino acids, or a mixture thereof. While L-amino acids represent the vast majority of amino acids found in proteins, D-amino acids are found in some proteins produced by exotic sea-dwelling organisms, such as cone snails. They are also abundant components of the peptidoglycan cell walls of bacteria. D-serine may act as a neurotransmitter in the brain. The L and D convention for amino acid configuration refers not to the optical activity of the amino acid itself, but rather to the optical activity of the isomer of glyceraldehyde from which that amino acid can theoretically be synthesized (D-glyceraldehyde is dextrorotary; L-glyceraldehyde is levorotary).

One form of an "all-D" peptide is a retro-inverso peptide. Retro-inverso modification of naturally-occurring polypeptides involves the synthetic assemblage of amino acids with α-carbon stereochemistry opposite to that of the corresponding L-amino acids, i.e., D-amino acids in reverse order with respect to the native peptide sequence. A retro-inverso analogue thus has reversed termini and reversed direction of peptide bonds (NH—CO rather than CO—NH) while approximately maintaining the topology of the side chains as in the native peptide sequence. See U.S. Pat. No. 6,261,569, incorporated herein by reference.

As mentioned above, the present invention contemplates fusing or conjugating a cell delivery domain (also called a cell delivery vector, or cell transduction domain). Such domains are well known in the art and are generally characterized as short amphipathic or cationic peptides and peptide derivatives, often containing multiple lysine and arginine resides (Fischer, 2007). Of particular interest are poly-D-Arg and poly-D-Lys sequences (e.g., dextrorotary residues, eight residues in length), while others are shown in Table 1, below.

TABLE 1

| CDD/CTD PEPTIDES | SEQ ID NO |
|---|---|
| QAATATRGRSAASRPTERPRAPARSASRPRRPVE | 2 |
| RQIKIWFQNRRMKWKK | 3 |
| RRMKWKK | 4 |
| RRWRRWWRRWWRRWRR | 5 |
| RGGRLSYSRRRFSTSTGR | 6 |
| YGRKKRRQRRR | 7 |
| RKKRRQRRR | 8 |
| YARAAARQARA | 9 |
| RRRRRRRR | 10 |
| KKKKKKKK | 11 |
| GWTLNSAGYLLGKINLKALAALAKXIL | 12 |
| LLILLRRRIRKQANAHSK | 13 |
| SRRHHCRSKAKRSRHH | 14 |
| NRARRNRRRVR | 15 |

TABLE 1-continued

| CDD/CTD PEPTIDES | SEQ ID NO |
|---|---|
| RQLRIAGRRLRGRSR | 16 |
| KLIKGRTPIKFGK | 17 |
| RRIPNRRPRR | 18 |
| KLALKLALKALKAALKLA | 19 |
| KLAKLAKKLAKLAK | 20 |
| GALFLGFLGAAGSTNGAWSQPKKKRKV | 21 |
| KETWWETWWTEWSQPKKKRKV | 22 |
| GALFLGWLGAAGSTMGAKKKRKV | 23 |
| MGLGLHLLVLAAALQGAKSKRKV | 24 |
| AAVALLPAVLLALLAPAAANYKKPKL | 25 |
| MANLGYWLLALFVTMWTDVGLCKKRPKP | 26 |
| LGTYTQDFNKFHTFPQTAIGVGAP | 27 |
| DPKGDPKGVTVTVTVTGKGDPXPD | 28 |
| PPPPPPPPPPPPPP | 29 |
| VRLPPPVRLPPPVRLPPP | 30 |
| PRPLPPPRPG | 31 |
| SVRRRPRPPYLPRPRPPPFFPPRLPPRIPP | 32 |
| TRSSRAGLQFPVGRVHRLLRK | 33 |
| GIGKFLHSAKKFGKAFVGEIMNS | 34 |
| KWKLFKKIEKVGQNIRDGIIKAGPAVAVVGQATQIAK | 35 |
| ALWMTLLKKVLKAAAKAALNAVLVGANA | 36 |
| GIGAVLKVLTTGLPALISWIKRKRQQ | 37 |
| INLKALAALAKKIL | 38 |
| GFFALIPKIISSPLPKTLLSAVGSALGGSGGQE | 39 |
| LAKWALKQGFAKLKS | 40 |
| SMAQDIISTIGDLVKWIIQTVNXFTKK | 41 |
| LLGDFFRKSKEKIGKEFKRIVQRIKQRIKDFLANLVPRTES | 42 |
| LKKLLKKLLKKLLKKLLKKL | 43 |
| KLKLKLKLKLKLKLKLKL | 44 |
| PAWRKAFRWAWRMLKKAA | 45 |

Also as mentioned above, peptides modified for in vivo use by the addition, at the amino- and/or carboxyl-terminal ends, of a blocking agent to facilitate survival of the peptide in vivo are contemplated. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. These agents can be added either chemically during the synthesis of the peptide, or by recombinant DNA technology by methods familiar in the art. Alternatively, blocking agents such as pyroglutamic acid or other molecules known in the art can be attached to the amino- and/or carboxyl-terminal residues.

B. Synthesis

It will be advantageous to produce peptides using the solid-phase synthetic techniques (Merrifield, 1963). Other peptide synthesis techniques are well known to those of skill in the art (Bodanszky et al., 1976; Peptide Synthesis, 1985; Solid Phase Peptide Synthelia, 1984). Appropriate protective groups for use in such syntheses will be found in the above texts, as well as in Protective Groups in Organic Chemistry, 1973. These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

Aside from the 20 standard amino acids can be used, there are a vast number of "non-standard" amino acids. Two of these can be specified by the genetic code, but are rather rare in proteins. Selenocysteine is incorporated into some proteins at a UGA codon, which is normally a stop codon. Pyrrolysine is used by some methanogenic archaea in enzymes that they use to produce methane. It is coded for with the codon UAG. Examples of non-standard amino acids that are not found in proteins include lanthionine, 2-aminoisobutyric acid, dehydroalanine and the neurotransmitter gamma-aminobutyric acid. Non-standard amino acids often occur as intermediates in the metabolic pathways for standard amino acids—for example ornithine and citrulline occur in the urea cycle, part of amino acid catabolism. Non-standard amino acids are usually formed through modifications to standard amino acids. For example, homocysteine is formed through the transsulfuration pathway or by the demethylation of methionine via the intermediate metabolite S-adenosyl methionine, while hydroxyproline is made by a posttranslational modification of proline.

C. Linkers

Linkers or cross-linking agents may be used to fuse MyBP-C peptides to other proteinaceous sequences. Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino-, sulfhydryl-, guanidino-, indole-, or carboxyl-specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

In another example, heterobifunctional cross-linking reagents and methods of using the cross-linking reagents are described in U.S. Pat. No. 5,889,155, specifically incorporated herein by reference in its entirety. The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides. In instances where a particular peptide does not contain a residue amenable for a given cross-linking reagent in its native sequence, conservative genetic or synthetic amino acid changes in the primary sequence can be utilized.

Another use of linkers in the context of peptides as therapeutics is the so-called "Stapled Peptide" technology of Aileron Therapeutics. The general approach for "stapling" a peptide is that two key residues within the peptide are modified by attachment of linkers through the amino acid side chains. Once synthesized, the linkers are connected through a catalyst, thereby creating a bridge the physically constrains the peptide into its native α-helical shape. In addition to helping retain the native structure needed to interact with a target molecule, this conformation also provides stability against peptidases as well as cell-permeating properties. U.S. Pat. Nos. 7,192,713 and 7,183,059, describing this technology, are hereby incorporated by reference. See also Schafmeister et al., 2000.

D. Design, Variants and Analogs

Having identified structures in MyBP-C interaction with myosin, the inventors also contemplate that variants of the sequences may be employed. For example, certain non-natural amino acids that satisfy the structural constraints of the sequences may be substituted without a loss, and perhaps with an improvement in, biological function. In addition, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Methods for generating specific structures have been disclosed in the art. For example, α-helix mimetics are disclosed in U.S. Pat. Nos. 5,446,128; 5,710,245; 5,840,833; and 5,859,184. Methods for generating conformationally restricted β-turns and β-bulges are described, for example, in U.S. Pat. Nos. 5,440,013; 5,618,914; and 5,670,155. Other types of mimetic turns include reverse and γ-turns. Reverse turn mimetics are disclosed in U.S. Pat. Nos. 5,475,085 and 5,929,237, and γ-turn mimetics are described in U.S. Pat. Nos. 5,672,681 and 5,674,976.

As used herein, "molecular modeling" means quantitative and/or qualitative analysis of the structure and function of protein-protein physical interaction based on three-dimensional structural information and protein-protein interaction models. This includes conventional numeric-based molecular dynamic and energy minimization models, interactive computer graphic models, modified molecular mechanics models, distance geometry and other structure-based constraint models. Molecular modeling typically is performed using a computer and may be further optimized using known methods. Computer programs that use X-ray crystallography data are particularly useful for designing such compounds. Programs such as RasMol, for example, can be used to generate three dimensional models. Computer programs such as INSIGHT (Accelrys, Burlington, Mass.), GRASP (Anthony Nicholls, Columbia University), Dock (Molecular Design Institute, University of California at San Francisco), and Auto-Dock (Accelrys) allow for further manipulation and the ability to introduce new structures. The methods can involve the additional step of outputting to an output device a model of the 3-D structure of the compound. In addition, the 3-D data of candidate compounds can be compared to a computer database of, for example, 3-D structures.

Compounds of the invention also may be interactively designed from structural information of the compounds described herein using other structure-based design/modeling techniques (see, e.g., Jackson, 1997; Jones et al., 1996). Candidate compounds can then be tested in standard assays familiar to those skilled in the art. Exemplary assays are described herein.

The 3-D structure of biological macromolecules (e.g., proteins, nucleic acids, carbohydrates, and lipids) can be determined from data obtained by a variety of methodologies. These methodologies, which have been applied most effectively to the assessment of the 3-D structure of proteins, include: (a) x-ray crystallography; (b) nuclear magnetic resonance (NMR) spectroscopy; (c) analysis of physical distance constraints formed between defined sites on a macromolecule, e.g., intramolecular chemical crosslinks between residues on a protein (e.g., PCT/US00/14667, the disclosure of which is incorporated herein by reference in its entirety), and (d) molecular modeling methods based on a knowledge of the primary structure of a protein of interest, e.g., homology modeling techniques, threading algorithms, or ab initio structure modeling using computer programs such as MONSSTER (Modeling Of New Structures from Secondary and Tertiary Restraints) (see, e.g., International Application No. PCT/US99/11913, the disclosure of which is incorporated herein by reference in its entirety). Other molecular modeling techniques may also be employed in accordance with this invention (e.g., Cohen et al., 1990; Navia et al., 1992), the disclosures of which are incorporated herein by reference in their entirety). All these methods produce data that are amenable to computer analysis. Other spectroscopic methods that can also be useful in the method of the invention, but that do not currently provide atomic level structural detail about biomolecules, include circular dichroism and fluorescence and ultraviolet/visible light absorbance spectroscopy. A preferred method of analysis is x-ray crystallography. Descriptions of this procedure and of NMR spectroscopy are provided below.

X-ray Crystallography.

X-ray crystallography is based on the diffraction of x-radiation of a characteristic wavelength by electron clouds surrounding the atomic nuclei in a crystal of a molecule or molecular complex of interest. The technique uses crystals of purified biological macromolecules or molecular complexes (but these frequently include solvent components, co-factors, substrates, or other ligands) to determine near atomic resolution of the atoms making up the particular biological macromolecule. A prerequisite for solving 3-D structure by x-ray crystallography is a well-ordered crystal that will diffract x-rays strongly. The method directs a beam of x-rays onto a regular, repeating array of many identical molecules so that the x-rays are diffracted from the array in a pattern from which the structure of an individual molecule can be retrieved. Well-ordered crystals of, for example, globular protein molecules are large, spherical or ellipsoidal objects with irregular surfaces. The crystals contain large channels between the individual molecules. These channels, which normally occupy more than one half the volume of the crystal, are filled with disordered solvent molecules, and the protein molecules are in contact with each other at only a few small regions. This is one reason why structures of proteins in crystals are generally the same as those of proteins in solution.

Methods of obtaining the proteins of interest are described below. The formation of crystals is dependent on a number of different parameters, including pH, temperature, the concentration of the biological macromolecule, the nature of the solvent and precipitant, as well as the presence of added ions or ligands of the protein. Many routine crystallization experiments may be needed to screen all these parameters for the combinations that give a crystal suitable for x-ray diffraction analysis. Crystallization robots can automate and speed up work of reproducibly setting up a large number of crystallization experiments (see, e.g., U.S. Pat. No. 5,790,421, the disclosure of which is incorporated herein by reference in its entirety).

Polypeptide crystallization occurs in solutions in which the polypeptide concentration exceeds its solubility maximum (i.e., the polypeptide solution is supersaturated). Such solutions may be restored to equilibrium by reducing the polypeptide concentration, preferably through precipitation of the polypeptide crystals. Often polypeptides may be induced to crystallize from supersaturated solutions by adding agents that alter the polypeptide surface charges or perturb the interaction between the polypeptide and bulk water to promote associations that lead to crystallization.

Crystallizations are generally carried out between 4° C. and 20° C. Substances known as "precipitants" are often used to decrease the solubility of the polypeptide in a concentrated solution by forming an energetically unfavorable precipitating depleted layer around the polypeptide molecules (Weber, 1991). In addition to precipitants, other materials are sometimes added to the polypeptide crystallization solution. These include buffers to adjust the pH of the solution and salts to reduce the solubility of the polypeptide. Various precipitants are known in the art and include the following: ethanol, 3-ethyl-2-4 pentanediol, and many of the polyglycols, such as polyethylene glycol (PEG). The precipitating solutions can include, for example, 13-24% PEG 4000, 5-41% ammonium sulfate, and 1.0-1.5 M sodium chloride, and a pH ranging from 5.0-7.5. Other additives can include 0.1M Hepes, 2-4% butanol, 20-100 mM sodium acetate, 50-70 mM citric acid, 120-130 mM sodium phosphate, 1 mM ethylene diamine tetraacetic acid (EDTA), and 1 mM dithiothreitol (DTT). These agents are prepared in buffers and are added dropwise in various combinations to the crystallization buffer. Proteins to be crystallized can be modified, e.g., by phosphorylation or by using a phosphate mimic (e.g., tungstate, cacodylate, or sulfate).

Commonly used polypeptide crystallization methods include the following techniques: batch, hanging drop, seed initiation, and dialysis. In each of these methods, it is important to promote continued crystallization after nucleation by maintaining a supersaturated solution. In the batch method, polypeptide is mixed with precipitants to achieve supersaturation, and the vessel is sealed and set aside until crystals appear. In the dialysis method, polypeptide is retained in a sealed dialysis membrane that is placed into a solution containing precipitant. Equilibration across the membrane increases the polypeptide and precipitant concentrations, thereby causing the polypeptide to reach supersaturation levels.

In the hanging drop technique (McPherson, 1976), an initial polypeptide mixture is created by adding a precipitant to a concentrated polypeptide solution. The concentrations of the polypeptide and precipitants are such that in this initial form, the polypeptide does not crystallize. A small drop of this mixture is placed on a glass slide that is inverted and suspended over a reservoir of a second solution. The system is then sealed. Typically, the second solution contains a higher concentration of precipitant or other dehydrating agent. The difference in the precipitant concentrations causes the protein solution to have a higher vapor pressure than the second solution. Since the system containing the two solutions is sealed, an equilibrium is established, and water from the polypeptide mixture transfers to the second solution. This equilibrium increases the polypeptide and precipitant concentration in the polypeptide solution. At the critical concentration of polypeptide and precipitant, a crystal of the polypeptide may form.

Another method of crystallization introduces a nucleation site into a concentrated polypeptide solution. Generally, a concentrated polypeptide solution is prepared and a seed crystal of the polypeptide is introduced into this solution. If the concentrations of the polypeptide and any precipitants are correct, the seed crystal will provide a nucleation site around which a larger crystal forms.

Yet another method of crystallization is an electrocrystallization method in which use is made of the dipole moments of protein macromolecules that self-align in the Helmholtz layer adjacent to an electrode (see, e.g., U.S. Pat. No. 5,597,457, the disclosure of which is incorporated herein by reference in its entirety).

Some proteins may be recalcitrant to crystallization. However, several techniques are available to the skilled artisan to induce crystallization. For example, the removal of flexible polypeptide segments at the amino or carboxyl terminal end of the protein may facilitate production of crystalline protein samples. Removal of such segments can be done using molecular biology techniques or treatment of the protein with proteases such as trypsin, chymotrypsin, or subtilisin.

In diffraction experiments, a narrow and parallel beam of x-rays is taken from the x-ray source and directed onto the crystal to produce diffracted beams. The incident primary beams cause damage to both the macromolecule and solvent molecules. The crystal is, therefore, cooled (e.g., to between −220° C. and −50° C.) to prolong its lifetime. The primary beam must strike the crystal from many directions to produce all possible diffraction spots, so the crystal is rotated in the beam during the experiment. The diffracted spots are recorded on a film or by an electronic detector. Exposed film has to be digitized and quantified in a scanning device, whereas the electronic detectors feed the signals they detect directly into a computer. Electronic area detectors significantly reduce the time required to collect and measure diffraction data. Each diffraction beam, which is recorded as a spot on film or a detector plate, is defined by three properties: the amplitude, which is measured from the intensity of the spot; the wavelength, which is set by the x-ray source; and the phase, which is lost in x-ray experiments. All three properties are needed for all of the diffracted beams in order to determine the positions of the atoms giving rise to the diffracted beams. One way of determining the phases is called Multiple Isomorphous Replacement (MIR), which requires the introduction of exogenous x-ray scatterers (e.g., heavy atoms such metal atoms) into the unit cell of the crystal. For a more detailed description of MIR, see U.S. Pat. No. 6,093,573 (column 15) the disclosure of which is incorporated herein by reference in its entirety.

Atomic coordinates refer to Cartesian coordinates (x, y, and z positions) derived from mathematical equations involving Fourier synthesis of data derived from patterns obtained via diffraction of a monochromatic beam of x-rays by the atoms (scattering centers) of biological macromolecule of interest in crystal form. Diffraction data are used to calculate electron density maps of repeating units in the crystal (unit cell). Electron density maps are used to establish the positions (atomic coordinates) of individual atoms within a crystal's unit cell. The absolute values of atomic coordinates convey spatial relationships between atoms because the absolute values ascribed to atomic coordinates can be changed by rotational and/or translational movement along x, y, and/or z axes, together or separately, while maintaining the same relative spatial relationships among atoms. Thus, a biological macromolecule (e.g., a protein) whose set of absolute atomic coordinate values can be rotationally or translationally adjusted to coincide with a set of prior determined values from an analysis of another sample is considered to have the same atomic coordinates as those obtained from the other sample.

Further details on x-ray crystallography can be obtained from co-pending U.S. Application No. 2005/0015232, U.S. Pat. No. 6,093,573 and International Application Nos. PCT/US99/18441, PCT/US99/11913, and PCT/US00/03745. The disclosures of all these patent documents are incorporated herein by reference in their entirety.

NMR Spectroscopy.

Whereas x-ray crystallography requires single crystals of a macromolecule of interest, NMR measurements are carried out in solution under near physiological conditions. However, NMR-derived structures are not as detailed as crystal-derived structures.

While the use of NMR spectroscopy was until relatively recently limited to the elucidation of the 3-D structure of relatively small molecules (e.g., proteins of 100-150 amino acid residues), recent advances including isotopic labeling of the molecule of interest and transverse relaxation-optimized spectroscopy (TROSY) have allowed the methodology to be extended to the analysis of much larger molecules, e.g., proteins with a molecular weight of 110 kDa (Wider, 2000).

NMR uses radio-frequency radiation to examine the environment of magnetic atomic nuclei in a homogeneous magnetic field pulsed with a specific radio frequency. The pulses perturb the nuclear magnetization of those atoms with nuclei of nonzero spin. Transient time domain signals are detected as the system returns to equilibrium. Fourier transformation of the transient signal into a frequency domain yields a one-dimensional NMR spectrum. Peaks in these spectra represent chemical shifts of the various active nuclei. The chemical shift of an atom is determined by its local electronic environment. Two-dimensional NMR experiments can provide information about the proximity of various atoms in the structure and in three dimensional space. Protein structures can be determined by performing a number of two- (and sometimes 3- or 4-) dimensional NMR experiments and using the resulting information as constraints in a series of protein folding simulations.

More information on NMR spectroscopy including detailed descriptions of how raw data obtained from an NMR experiment can be used to determine the 3-D structure of a macromolecule can be found in: Protein NMR Spectroscopy, Principles and Practice, (1996); Gronenborn et al. (1990); and Wider (2000), supra., the disclosures of all of which are incorporated herein by reference in their entirety Also of interest are peptidomimetic compounds that are designed based upon the amino acid sequences of compounds of the invention that are peptides. Peptidomimetic compounds are synthetic compounds having a three-dimensional conformation "motif" that is substantially the same as the three-dimensional conformation of a selected peptide. The peptide motif provides the peptidomimetic compound with the ability to inhibit the interaction of $\alpha 6\beta 4$ and HER2 or EGFR. Peptidomimetic compounds can have additional characteristics that enhance their in vivo utility, such as increased cell permeability and prolonged biological half-life. The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

IV. METHODS OF TREATING HEART FAILURE

A. Therapeutic Regimens

Current medical management of cardiac hypertrophy in the setting of a cardiovascular disorder includes the use of at least two types of drugs: inhibitors of the rennin-angiotensoin system, and $\beta$-adrenergic blocking agents (Bristow, 1999). Therapeutic agents to treat pathologic hypertrophy in the setting of heart failure include angiotensin II converting enzyme (ACE) inhibitors and $\beta$-adrenergic receptor blocking agents (Eichhorn and Bristow, 1996). Other pharmaceutical agents that have been disclosed for treatment of cardiac hypertrophy include angiotensin II receptor antagonists (U.S. Pat. No. 5,604,251) and neuropeptide Y antagonists (WO 98/33791). Despite currently available pharmaceutical compounds, prevention and treatment of cardiac hypertrophy, and subsequent heart failure, continue to present a therapeutic challenge.

Non-pharmacological treatment is primarily used as an adjunct to pharmacological treatment. One means of non-pharmacological treatment involves reducing the sodium in the diet. In addition, non-pharmacological treatment also entails the elimination of certain precipitating drugs, including negative inotropic agents (e.g., certain calcium channel blockers and antiarrhythmic drugs like disopyramide), cardiotoxins (e.g., amphetamines), and plasma volume expanders (e.g., nonsteroidal anti-inflammatory agents and glucocorticoids).

In one embodiment of the present invention, methods for the treatment of heart failure utilizing inhibitors as described herein. For the purposes of the present application, treatment comprises reducing one or more of the symptoms of cardiac hypertrophy, such as reduced exercise capacity, reduced blood ejection volume, increased left ventricular end diastolic pressure, increased pulmonary capillary wedge pressure, reduced cardiac output, cardiac index, increased pulmonary artery pressures, increased left ventricular end systolic and diastolic dimensions, and increased left ventricular wall stress, wall tension and wall thickness-same for right ventricle. In addition, use of the disclosed inhibitors may delay development of year failure.

Treatment regimens would vary depending on the clinical situation. However, long term maintenance would appear to be appropriate in most circumstances. It also may be desirable treat hypertrophy with the disclosed inhibitors intermittently, such as within brief window during disease progression.

B. Combined Therapy

In another embodiment, it is envisioned to use an inhibitor as described herein combination with other therapeutic modalities. Thus, in addition to the therapies described above, one may also provide to the patient more "standard" pharmaceutical cardiac therapies. Examples of other therapies include, without limitation, so-called "beta blockers," anti-hypertensives, cardiotonics, anti-thrombotics, vasodilators, hormone antagonists, iontropes, diuretics, endothelin antagonists, calcium channel blockers, phosphodiesterase inhibitors, ACE inhibitors, angiotensin type 2 antagonists and cytokine blockers/inhibitors, and HDAC inhibitors.

Combinations may be achieved by contacting cardiac cells with a single composition or pharmacological formulation that includes both agents, or by contacting the cell with two distinct compositions or formulations, at the same time, wherein one composition includes the expression construct and the other includes the agent. Alternatively, the therapy using the inhibitors of the present invention may precede or follow administration of the other agent(s) by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would typically contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either an inhibitor according to the present invention, or the other agent will be desired. In this regard, various combinations may be employed. By way of illustration, where the inhibitor of according to the present invention is "A" and the other agent is "B", the following permutations based on 3 and 4 total administrations are exemplary:

A/B/A B/A/B B/B/A A/A/B B/A/A A/B/B B/B/B/A B/B/ A/B A/A/B/B A/B/A/B A/B/B/A B/B/A/A B/A/B/A B/A/A/B B/B/B/A A/A/A/B B/A/A/A A/B/A/A A/A/ B/A A/B/B/B B/A/B/B B/B/A/B

Other combinations are likewise contemplated.

C. Pharmacological Therapeutic Agents

Pharmacological therapeutic agents and methods of administration, dosages, etc., are well known to those of skill in the art (see for example, the "Physicians Desk Reference," Klaassen's "The Pharmacological Basis of Therapeutics," "Remington's Pharmaceutical Sciences," and "The Merck Index, Eleventh Edition," incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

Non-limiting examples of a pharmacological therapeutic agent that may be used in the present invention include an antihyperlipoproteinemic agent, an antiarteriosclerotic agent, an antithrombotic/fibrinolytic agent, a blood coagulant, an antiarrhythmic agent, an antihypertensive agent, a vasopressor, a treatment agent for congestive heart failure, an antianginal agent, an antibacterial agent or a combination thereof.

In addition, it should be noted that any of the following may be used to develop new sets of cardiac therapy target genes as β-blockers were used in the present examples (see below). While it is expected that many of these genes may overlap, new gene targets likely can be developed.

i. Antihyperlipoproteinemics

In certain embodiments, administration of an agent that lowers the concentration of one of more blood lipids and/or lipoproteins, known herein as an "antihyperlipoproteinemic," may be combined with a cardiovascular therapy according to the present invention, particularly in treatment of athersclerosis and thickenings or blockages of vascular tissues. In certain aspects, an antihyperlipoproteinemic agent may comprise an aryloxyalkanoic/fibric acid derivative, a resin/bile acid sequesterant, a HMG CoA reductase inhibitor, a nicotinic acid derivative, a thyroid hormone or thyroid hormone analog, a miscellaneous agent or a combination thereof.

a. Aryloxyalkanoic Acid/Fibric Acid Derivatives

Non-limiting examples of aryloxyalkanoic/fibric acid derivatives include beclobrate, enzafibrate, binifibrate, ciprofibrate, clinofibrate, clofibrate (atromide-S), clofibric acid, etofibrate, fenofibrate, gemfibrozil (lobid), nicofibrate, pirifibrate, ronifibrate, simfibrate and theofibrate.

b. Resins/Bile Acid Sequesterants

Non-limiting examples of resins/bile acid sequesterants include cholestyramine (cholybar, questran), colestipol (colestid) and polidexide.

c. HMG CoA Reductase Inhibitors

Non-limiting examples of HMG CoA reductase inhibitors include lovastatin (mevacor), pravastatin (pravochol) or simvastatin (zocor).

d. Nicotinic Acid Derivatives

Non-limiting examples of nicotinic acid derivatives include nicotinate, acepimox, niceritrol, nicoclonate, nicomol and oxiniacic acid.

e. Thyroid Hormones and Analogs

Non-limiting examples of thyroid hormones and analogs thereof include etoroxate, thyropropic acid and thyroxine.

f. Miscellaneous Antihyperlipoproteinemics

Non-limiting examples of miscellaneous antihyperlipoproteinemics include acifran, azacosterol, benfluorex, β-benzalbutyramide, carnitine, chondroitin sulfate, clomestrone, detaxtran, dextran sulfate sodium, 5,8,11,14,17-eicosapentaenoic acid, eritadenine, furazabol, meglutol, melinamide, mytatrienediol, ornithine, γ-oryzanol, pantethine, pentaerythritol tetraacetate, α-phenylbutyramide, pirozadil, probucol (lorelco), β-sitosterol, sultosilic acid-piperazine salt, tiadenol, triparanol and xenbucin.

ii. Antiarteriosclerotics

Non-limiting examples of an antiarteriosclerotic include pyridinol carbamate.

iii. Antithrombotic/Fibrinolytic Agents

In certain embodiments, administration of an agent that aids in the removal or prevention of blood clots may be combined with administration of a modulator, particularly in treatment of atherosclerosis and vasculature (e.g., arterial) blockages. Non-limiting examples of antithrombotic and/or fibrinolytic agents include anticoagulants, anticoagulant antagonists, antiplatelet agents, thrombolytic agents, thrombolytic agent antagonists or combinations thereof.

In certain aspects, antithrombotic agents that can be administered orally, such as, for example, aspirin and wafarin (coumadin), are preferred.

a. Anticoagulants

A non-limiting example of an anticoagulant include acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin.

b. Antiplatelet Agents

Non-limiting examples of antiplatelet agents include aspirin, a dextran, dipyridamole (persantin), heparin, sulfinpyranone (anturane) and ticlopidine (ticlid).

c. Thrombolytic Agents

Non-limiting examples of thrombolytic agents include tissue plaminogen activator (activase), plasmin, pro-urokinase, urokinase (abbokinase) streptokinase (streptase), anistreplase/APSAC (eminase).

iv. Blood Coagulants

In certain embodiments wherein a patient is suffering from a hemorrhage or an increased likelihood of hemorrhaging, an agent that may enhance blood coagulation may be used. Non-limiting examples of a blood coagulation promoting agent include thrombolytic agent antagonists and anticoagulant antagonists.

a. Anticoagulant Antagonists

Non-limiting examples of anticoagulant antagonists include protamine and vitamine K1.

b. Thrombolytic Agent Antagonists and Antithrombotics

Non-limiting examples of thrombolytic agent antagonists include amiocaproic acid (amicar) and tranexamic acid (amstat). Non-limiting examples of antithrombotics include anagrelide, argatroban, cilstazol, daltroban, defibrotide, enoxaparin, fraxiparine, indobufen, lamoparan, ozagrel, picotamide, plafibride, tedelparin, ticlopidine and triflusal.

v. Antiarrhythmic Agents

Non-limiting examples of antiarrhythmic agents include Class I antiarrythmic agents (sodium channel blockers), Class II antiarrhythmic agents (beta-adrenergic blockers), Class II antiarrhythmic agents (repolarization prolonging drugs), Class IV antiarrythmic agents (calcium channel blockers) and miscellaneous antiarrythmic agents.

a. Sodium Channel Blockers

Non-limiting examples of sodium channel blockers include Class IA, Class IB and Class IC antiarrhythmic agents. Non-limiting examples of Class IA antiarrhythmic agents include disppyramide (norpace), procainamide (pronestyl) and quinidine (quinidex). Non-limiting examples of Class IB antiarrhythmic agents include lidocaine (xylocaine), tocamide (tonocard) and mexiletine (mexitil). Non-limiting examples of Class IC antiarrhythmic agents include encamide (enkaid) and flecamide (tambocor).

b. Beta Blockers

Non-limiting examples of a beta blocker, otherwise known as a β-adrenergic blocker, a β-adrenergic antagonist or a Class II antiarrhythmic agent, include acebutolol (sectral), alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol (brevibloc), indenolol, labetalol, levobunolol, mepindolol, metipranolol, metoprolol, moprolol, nadolol, nadoxolol, nifenalol, nipradilol, oxprenolol, penbutolol, pindolol, practolol, pronethalol, propanolol (inderal), sotalol (betapace), sulfinalol, talinolol, tertatolol, timolol, toliprolol and xibinolol. In certain aspects, the beta blocker comprises an aryloxypropanolamine derivative. Non-limiting examples of aryloxypropanolamine derivatives include acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, moprolol, nadolol, nipradilol, oxprenolol, penbutolol, pindolol, propanolol, talinolol, tertatolol, timolol and toliprolol.

c. Repolarization Prolonging Agents

Non-limiting examples of an agent that prolong repolarization, also known as a Class III antiarrhythmic agent, include amiodarone (cordarone) and sotalol (betapace).

d. Calcium Channel Blockers/Antagonist

Non-limiting examples of a calcium channel blocker, otherwise known as a Class IV antiarrythmic agent, include an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazinde derivative (e.g., cinnarizine, flunarizine, lidoflazine) or a micellaneous calcium channel blocker such as bencyclane, etafenone, magnesium, mibefradil or perhexyline. In certain embodiments a calcium channel blocker comprises a long-acting dihydropyridine (nifedipine-type) calcium antagonist.

e. Miscellaneous Antiarrhythmic Agents

Non-limiting examples of miscellaneous antiarrhymic agents include adenosine (adenocard), digoxin (lanoxin), acecamide, ajmaline, amoproxan, aprindine, bretylium tosylate, bunaftine, butobendine, capobenic acid, cifenline, disopyranide, hydroquinidine, indecamide, ipatropium bromide, lidocaine, lorajmine, lorcamide, meobentine, moricizine, pirmenol, prajmaline, propafenone, pyrinoline, quinidine polygalacturonate, quinidine sulfate and viquidil.

vi. Antihypertensive Agents

Non-limiting examples of antihypertensive agents include sympatholytic, alpha/beta blockers, alpha blockers, anti-angiotensin II agents, beta blockers, calcium channel blockers, vasodilators and miscellaneous antihypertensives.

a. Alpha Blockers

Non-limiting examples of an alpha blocker, also known as an α-adrenergic blocker or an α-adrenergic antagonist, include amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an alpha blocker may comprise a quinazoline derivative. Non-limiting examples of quinazoline derivatives include alfuzosin, bunazosin, doxazosin, prazosin, terazosin and trimazosin.

b. Alpha/Beta Blockers

In certain embodiments, an antihypertensive agent is both an alpha and beta adrenergic antagonist. Non-limiting examples of an alpha/beta blocker comprise labetalol (normodyne, trandate).

c. Anti-Angiotension II Agents

Non-limiting examples of anti-angiotension II agents include angiotensin converting enzyme inhibitors and angiotension II receptor antagonists. Non-limiting examples of angiotension converting enzyme inhibitors (ACE inhibitors) include alacepril, enalapril (vasotec), captopril, cilazapril, delapril, enalaprilat, fosinopril, lisinopril, moveltopril, perindopril, quinapril and ramipril. Non-limiting examples of an angiotensin II receptor blocker, also known as an angiotension II receptor antagonist, an ANG receptor blocker or an ANG-II type-1 receptor blocker (ARBS), include angiocandesartan, eprosartan, irbesartan, losartan and valsartan.

d. Sympatholytics

Non-limiting examples of a sympatholytic include a centrally acting sympatholytic or a peripherally acting sympatholytic. Non-limiting examples of a centrally acting sympatholytic, also known as an central nervous system (CNS) sympatholytic, include clonidine (catapres), guanabenz (wytensin) guanfacine (tenex) and methyldopa (aldomet). Non-limiting examples of a peripherally acting sympatholytic include a ganglion blocking agent, an adrenergic neuron blocking agent, a β-adrenergic blocking agent or a alpha1-adrenergic blocking agent. Non-limiting examples of a ganglion blocking agent include mecamylamine (inversine) and trimethaphan (arfonad). Non-limiting of an adrenergic neuron blocking agent include guanethidine (ismelin) and reserpine (serpasil). Non-limiting examples of a β-adrenergic blocker include acenitolol (sectral), atenolol (tenormin), betaxolol (kerlone), carteolol (cartrol), labetalol (normodyne, trandate), metoprolol (lopressor), nadanol (corgard), penbutolol (levatol), pindolol (visken), propranolol (inderal) and timolol (blocadren). Non-limiting examples of alpha1-adrenergic blocker include prazosin (minipress), doxazocin (cardura) and terazosin (hytrin).

e. Vasodilators

In certain embodiments a cardiovasculator therapeutic agent may comprise a vasodilator (e.g., a cerebral vasodilator, a coronary vasodilator or a peripheral vasodilator). In certain preferred embodiments, a vasodilator comprises a coronary vasodilator. Non-limiting examples of a coronary vasodilator include amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(β-diethylaminoethyl ether), hexobendine, itramin tosylate, khellin, lidoflanine, mannitol hexanitrane, medibazine, nicorglycerin, pentaerythritol tetranitrate, pentrinitrol, perhexyline, pimethylline, trapidil, tricromyl, trimetazidine, trolnitrate phosphate and visnadine.

In certain aspects, a vasodilator may comprise a chronic therapy vasodilator or a hypertensive emergency vasodilator. Non-limiting examples of a chronic therapy vasodilator include hydralazine (apresoline) and minoxidil (loniten). Non-limiting examples of a hypertensive emergency vasodilator include nitroprusside (nipride), diazoxide (hyperstat IV), hydralazine (apresoline), minoxidil (loniten) and verapamil.

f. Miscellaneous Antihypertensives

Non-limiting examples of miscellaneous antihypertensives include ajmaline, γ-aminobutyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzolimine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil.

In certain aspects, an antihypertensive may comprise an arylethanolamine derivative, a benzothiadiazine derivative, a N-carboxyalkyl(peptide/lactam) derivative, a dihydropyridine derivative, a guanidine derivative, a hydrazines/phthalazine, an imidazole derivative, a quanternary ammonium compound, a reserpine derivative or a suflonamide derivative.

Arylethanolamine Derivatives.

Non-limiting examples of arylethanolamine derivatives include amosulalol, bufuralol, dilevalol, labetalol, pronethalol, sotalol and sulfinalol.

Benzothiadiazine Derivatives.

Non-limiting examples of benzothiadiazine derivatives include althizide, bendroflumethiazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothizide, hydroflumethizide, methyclothiazide, meticrane, metolazone, paraflutizide, polythizide, tetrachlormethiazide and trichlormethiazide.

N-Carboxyalkyl(Peptide/Lactam) Derivatives.

Non-limiting examples of N-carboxyalkyl(peptide/lactam) derivatives include alacepril, captopril, cilazapril, delapril, enalapril, enalaprilat, fosinopril, lisinopril, moveltipril, perindopril, quinapril and ramipril.

Dihydropyridine Derivatives.

Non-limiting examples of dihydropyridine derivatives include amlodipine, felodipine, isradipine, nicardipine, nifedipine, nilvadipine, nisoldipine and nitrendipine.

Guanidine Derivatives.

Non-limiting examples of guanidine derivatives include bethanidine, debrisoquin, guanabenz, guanacline, guanadrel, guanazodine, guanethidine, guanfacine, guanochlor, guanoxabenz and guanoxan.

Hydrazines/Phthalazines.

Non-limiting examples of hydrazines/phthalazines include budralazine, cadralazine, dihydralazine, endralazine, hydracarbazine, hydralazine, pheniprazine, pildralazine and todralazine.

Imidazole Derivatives.

Non-limiting examples of imidazole derivatives include clonidine, lofexidine, phentolamine, tiamenidine and tolonidine.

Quanternary Ammonium Compounds.

Non-limiting examples of quanternary ammonium compounds include azamethonium bromide, chlorisondamine chloride, hexamethonium, pentacynium bis(methylsulfate), pentamethonium bromide, pentolinium tartrate, phenactropinium chloride and trimethidinium methosulfate.

Reserpine Derivatives.

Non-limiting examples of reserpine derivatives include bietaserpine, deserpidine, rescinnamine, reserpine and syrosingopine.

Suflonamide Derivatives.

Non-limiting examples of sulfonamide derivatives include ambuside, clopamide, furosemide, indapamide, quinethazone, tripamide and xipamide.

g. Vasopressors

Vasopressors generally are used to increase blood pressure during shock, which may occur during a surgical procedure. Non-limiting examples of a vasopressor, also known as an antihypotensive, include amezinium methyl sulfate, angiotensin amide, dimetofrine, dopamine, etifelmin, etilefrin, gepefrine, metaraminol, midodrine, norepinephrine, pholedrine and Synephrine.

vii. Treatment Agents for Congestive Heart Failure

Non-limiting examples of agents for the treatment of congestive heart failure include anti-angiotension II agents, afterload-preload reduction treatment, diuretics and inotropic agents.

a. Afterload-Preload Reduction

In certain embodiments, an animal patient that can not tolerate an angiotension antagonist may be treated with a combination therapy. Such therapy may combine administration of hydralazine (apresoline) and isosorbide dinitrate (isordil, sorbitrate).

b. Diuretics

Non-limiting examples of a diuretic include a thiazide or benzothiadiazine derivative (e.g., althiazide, bendroflumethazide, benzthiazide, benzylhydrochlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlormerodrin, meralluride, mercamphamide, mercaptomerin sodium, mercumallylic acid, mercumatilin dodium, mercurous chloride, mersalyl), a pteridine (e.g., furtherene, triamterene), purines (e.g., acefylline, 7-morpholinomethyltheophylline, pamobrom, protheobromine, theobromine), steroids including aldosterone antagonists (e.g., canrenone, oleandrin, spironolactone), a sulfonamide derivative (e.g., acetazolamide, ambuside, azosemide, bumetanide, butazolamide, chloraminophenamide, clofenamide, clopamide, clorexolone, diphenylmethane-4,4'-disulfonamide, disulfamide, ethoxzolamide, furosemide, indapamide, mefruside, methazolamide, piretanide, quinethazone, torasemide, tripamide, xipamide), a uracil (e.g., aminometradine, amisometradine), a potassium sparing antagonist (e.g., amiloride, triamterene) or a miscellaneous diuretic such as aminozine, arbutin, chlorazanil, ethacrynic acid, etozolin, hydracarbazine, isosorbide, mannitol, metochalcone, muzolimine, perhexyline, ticrnafen and urea.

c. Inotropic Agents

Non-limiting examples of a positive inotropic agent, also known as a cardiotonic, include acefylline, an acetyldigitoxin, 2-amino-4-picoline, amrinone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythrophleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol.

In particular aspects, an intropic agent is a cardiac glycoside, a beta-adrenergic agonist or a phosphodiesterase inhibitor. Non-limiting examples of a cardiac glycoside includes digoxin (lanoxin) and digitoxin (crystodigin). Non-limiting examples of a β-adrenergic agonist include albuterol, bambuterol, bitolterol, carbuterol, clenbuterol, clorprenaline, denopamine, dioxethedrine, dobutamine (dobutrex), dopamine (intropin), dopexamine, ephedrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Non-limiting examples of a phosphodiesterase inhibitor include aminone (inocor).

d. Antianginal Agents

Antianginal agents may comprise organonitrates, calcium channel blockers, beta blockers and combinations thereof.

Non-limiting examples of organonitrates, also known as nitrovasodilators, include nitroglycerin (nitro-bid, nitrostat), isosorbide dinitrate (isordil, sorbitrate) and amyl nitrate (aspirol, vaporole).

D. Surgical Therapeutic Agents

In certain aspects, the secondary therapeutic agent may comprise a surgery of some type, which includes, for example, preventative, diagnostic or staging, curative and palliative surgery. Surgery, and in particular a curative surgery, may be used in conjunction with other therapies, such as the present invention and one or more other agents.

Such surgical therapeutic agents for vascular and cardiovascular diseases and disorders are well known to those of skill in the art, and may comprise, but are not limited to, performing surgery on an organism, providing a cardiovascular mechanical prostheses, angioplasty, coronary artery reperfusion, catheter ablation, providing an implantable cardioverter defibrillator to the subject, mechanical circulatory support or a combination thereof. Non-limiting examples of a mechanical circulatory support that may be used in the present invention comprise an intra-aortic balloon counterpulsation, left ventricular assist device or combination thereof.

E. Drug Formulations and Routes for Administration to Patients

Where clinical applications are contemplated, pharmaceutical compositions will be prepared in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector or cells, dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or cells of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal or intravenous injection, or by direct injection into cardiac tissue. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

For oral administration the polypeptides of the present invention generally may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety, and purity standards as required by FDA Office of Biologics standards.

V. PURIFICATION OF PEPTIDES/PROTEINS

It will be desirable to purify peptides and polypeptides according to the present invention. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

VI. DEFINITIONS

As used herein, the term "heart failure" is broadly used to mean any condition that reduces the ability of the heart to pump blood. As a result, congestion and edema develop in the tissues. Most frequently, heart failure is caused by decreased contractility of the myocardium, resulting from reduced coronary blood flow; however, many other factors may result in heart failure, including damage to the heart valves, vitamin deficiency, and primary cardiac muscle disease. Though the precise physiological mechanisms of heart failure are not entirely understood, heart failure is generally believed to involve disorders in several cardiac autonomic properties, including sympathetic, parasympathetic, and baroreceptor responses. The phrase "manifestations of heart failure" is used broadly to encompass all of the sequelae associated with heart failure, such as shortness of breath, pitting edema, an enlarged tender liver, engorged neck veins, pulmonary rales and the like including laboratory findings associated with heart failure.

The term "treatment" or grammatical equivalents encompasses the improvement and/or reversal of the symptoms of heart failure (i.e., the ability of the heart to pump blood). "Improvement in the physiologic function" of the heart may be assessed using any of the measurements described herein (e.g., measurement of ejection fraction, fractional shortening, left ventricular internal dimension, heart rate, etc.), as well as any effect upon the animal's survival. In use of animal models, the response of treated transgenic animals and untreated transgenic animals is compared using any of the assays described herein (in addition, treated and untreated non-transgenic animals may be included as controls). A compound which causes an improvement in any parameter associated with heart failure used in the screening methods of the instant invention may thereby be identified as a therapeutic compound.

The term "dilated cardiomyopathy" refers to a type of heart failure characterized by the presence of a symmetrically dilated left ventricle with poor systolic contractile function and, in addition, frequently involves the right ventricle.

The term "compound" refers to any chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening using the screening methods of the present invention. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of heart failure.

As used herein, the term "cardiac hypertrophy" refers to the process in which adult cardiac myocytes respond to stress through hypertrophic growth. Such growth is characterized by cell size increases without cell division, assembling of additional sarcomeres within the cell to maximize force generation, and an activation of a fetal cardiac gene program. Cardiac hypertrophy is often associated with increased risk of morbidity and mortality, and thus studies aimed at understanding the molecular mechanisms of cardiac hypertrophy could have a significant impact on human health.

As used herein, the terms "antagonist" and "inhibitor" refer to molecules, compounds, or nucleic acids which inhibit the action of a cellular factor that may be involved in cardiac hypertrophy. Antagonists may or may not be homologous to these natural compounds in respect to conformation, charge or other characteristics. Thus, antagonists may be recognized by the same or different receptors that are recognized by an agonist. Antagonists may have allosteric effects which prevent the action of an agonist. Alternatively, antagonists may prevent the function of the agonist. In contrast to the agonists, antagonistic compounds do not result in pathologic and/or biochemical changes within the cell such that the cell reacts to the presence of the antagonist in the same manner as if the cellular factor was present. Antagonists and inhibitors may include proteins, nucleic acids, carbohydrates, or any other molecules which bind or interact with a receptor, molecule, and/or pathway of interest.

As used herein, the term "modulate" refers to a change or an alteration in a biological activity. Modulation may be an increase or a decrease in protein activity, a change in kinase activity, a change in binding characteristics, or any other change in the biological, functional, or immunological properties associated with the activity of a protein or other structure of interest. The term "modulator" refers to any molecule or compound which is capable of changing or altering biological activity as described above.

The term "β-adrenergic receptor antagonist" refers to a chemical compound or entity that is capable of blocking, either partially or completely, the beta (β) type of adrenoreceptors (i.e., receptors of the adrenergic system that respond to catecholamines, especially norepinephrine). Some β-adrenergic receptor antagonists exhibit a degree of specificity for one receptor sybtype (generally $β_1$); such antagonists are termed "$β_1$-specific adrenergic receptor antagonists" and "$β_2$-specific adrenergic receptor antagonists." The term β-adrenergic receptor antagonist" refers to chemical compounds that are selective and non-selective antagonists. Examples of β-adrenergic receptor antagonists include, but are not limited to, acebutolol, atenolol, butoxamine, carteolol, esmolol, labetolol, metoprolol, nadolol, penbutolol, propanolol, and timolol. The use of derivatives of known β-adrenergic receptor antagonists is encompassed by the methods of the present invention. Indeed any compound, which functionally behaves as a β-adrenergic receptor antagonist is encompassed by the methods of the present invention.

The terms "angiotensin-converting enzyme inhibitor" or "ACE inhibitor" refer to a chemical compound or entity that is capable of inhibiting, either partially or completely, the enzyme involved in the conversion of the relatively inactive angiotensin I to the active angiotensin II in the rennin-angiotensin system. In addition, the ACE inhibitors concomitantly inhibit the degradation of bradykinin, which likely significantly enhances the antihypertensive effect of the ACE inhibitors. Examples of ACE inhibitors include, but are not limited to, benazepril, captopril, enalopril, fosinopril, lisinopril, quiapril and ramipril. The use of derivatives of known ACE inhibitors is encompassed by the methods of the present invention. Indeed any compound, which functionally behaves as an ACE inhibitor, is encompassed by the methods of the present invention.

VII. EXAMPLES

The following examples are included to further illustrate various aspects of the invention. It should be appreciated by those of skill in the art that the techniques disclosed in the examples which follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Development of the Peptide Disruptor of cMyBP-C Binding to Myosin.

A myosin-binding peptide-based therapeutic agent has been identified based on the premise that disruption of the myosin-cMyBP-C interface would release a molecular brake on cardiomyocyte contractility imposed by the inhibitory activity of the unphosphorylated form of cMyBP-C on myosin. Since there is no PDB-reported structure for the 11-domain protein cMyBP-C, the molecular design of the peptide was developed on a sequence-based approximate prediction of a putative myosin-binding site. To predict the sequence of the peptide, the inventors sought a region between the C1 and C2 domains of cMyBP-C (which binds to myosin) in the twilight zone between order and disorder, using PONDR®, a predictor of native disorder (Pietrosemoli et al., 2007). The version used, PONDR-VLXT (Li et al., 1999), assigns a disorder propensity score D to each amino acid along the chain, with D=0 corresponding to certainty of order and D=1 corresponding to certainty of structural disorder. On the other hand, it is well established that regions in the twilight between order and disorder, with 0.35<D<0.8, are rich in structural defects known as "dehydrons," which signal local sites in the structure with solvent exposure of backbone hydrogen bonds. These regions are inherently sticky since dehydrons enhance their stability by promoting dehydration (Fernández, 2012), which in turn translates mechanically into an attractive drag on nonpolar groups.

A crucial twilight region containing phosphorylation sites S302, S307 was identified in the motif region intercalated between domains C1 and C2 of cMyBP-C, more precisely in the sequence region 293-310. Thus, the 18-unit region $_{293}$FSSLLKKRDSFRRDSKLE$_{310}$ (SEQ ID NO:46) was predicted as disordered in the 302,307-phosphorylated state but capable of a transition to an ordered state upon binding to myosin in the unphosphorylated state. This finding guided the molecular design of the peptide 302A: FSSLLKKRDAFRRDAKLE (SEQ ID NO:47), with S→A substitutions at positions 302 and 307. Peptide 302A becomes a surrogate for a myosin-binding region of cMyBP-C, susceptible to acquiring order upon binding to myosin, while incapable of being phosphorylated and thus reversing back to the unbound state. These properties provide the rationale for its therapeutic impact to treat heart failure, based on its competitive binding to myosin and concurrent release of the molecular brake on contractility by precluding binding of cMyBP-C.

The peptide was synthesized by a commercial vendor (UW Biotechnology Center) and delivered as a lyophilized powder. The peptide was dissolved in water and subsequently dialyzed against water to remove ionic contaminants, lyophilized and then dissolved in relaxing solution (below) for treatment of membrane permeabilized (skinned) preparations of murine and porcine myocardium.

Contractile Measurements.

The experimental methods used in testing the peptide disruptor of cMyBP-C binding to myosin are standard methods in the inventors' laboratory, as published previously (e.g., Chen et al., 2010).

Skinned Myocardial Preparations.

Skinned ventricular myocardium was prepared according to the protocol described by Chen et al. (2010). In brief, beating hearts were excised in vivo from anesthetized WT mice of either sex (~6 months old) and dissected in $Ca^{2+}$-Ringer's solution containing 120 mM NaCl, 19 mM NaHCO$_3$, 5 mM KCl, 1.2 mM Na$_2$HPO$_4$, 1.2 mM MgSO$_4$, 1 mM CaCl$_2$, and 10 mM glucose, pH 7.4 at 22° C., pre-equilibrated with 95% O$_2$/5% CO$_2$. Basal levels of RLC phosphorylation were reduced to uniformly low levels (i.e., <10%) as described previously (Olsson et al., 2004; Stelzer et al., 2006) by perfusing hemisected hearts with $Ca^{2+}$-Ringer's solution containing 30 mM 2,3-butanedione monoxime (BDM) for 30 minutes at 22° C. before rapid freezing in liquid nitrogen for storage prior to experimental measurements. The dephosphorylation of RLC provides an appropriate background for assessment of the effects of the peptide, since RLC phosphorylation increases force production in heart muscle and speeds contraction and RLC phosphorylation is nearly nil in heart failure.

On the day of an experiment, frozen ventricles were thawed and homogenized in ice-cold relaxing solution containing 100 mM KCl, 10 mM imidazole, 5 mM MgCl$_2$, 2 mM EGTA, and 4 mMATP, pH 7.0 at 22° C. to yield multicellular preparations with dimensions of 600-900 μm×100-250 μm using a Polytron homogenizer. The cellular homogenates were then centrifuged and subsequently resuspended in ice-cold relaxing solution containing 250 μg/ml saponin and 1% Triton X-100 for 30 minutes at 4° C. The cellular homogenates were centrifuged, washed with ice-cold relaxing solution several times and stored on ice until used in mechanical experiments.

Measurements of Force and the Kinetics of Force Development.

Skinned myocardial preparations were attached between a force transducer (for measurements of force) and a displacement motor (to impose rapid changes in length for measurements of the kinetics of force development) while in relaxing solution (Olsson et al., 2004). The temperature was then adjusted to 22° C. for measurements of the contractile properties of myocardium in the presence and absence of peptide.

The force generating properties of murine or porcine skinned myocardium were measured as a function of free [$Ca^{2+}$] in activating solutions containing salts, a $Ca^{2+}$ buffer, and MgATP (Olsson et al., 2004). Free $Ca^{2+}$, expressed as $-\log[Ca^{2+}]_{free}$, was varied between sub-threshold (pCa 7.0) and saturating (pCa 4.5) levels with respect to force development. Measurements of isometric force as a function of pCa yielded force-pCa relationships, from which was determined the $Ca^{2+}$ sensitivity of force defined as the pCa at which force was half-maximal.

The kinetics of force development were assessed as a function of pCa by measuring the rate of force redevelopment at each pCa following a rapid slackening and re-stretch of the muscle during steady $Ca^{2+}$ activation (Olsson et al., 2004; Stelzer et al., 2006). Fitting an exponential curve to the time-course of force redevelopment following this sequence of length changes yielded a rate constant of force redevelopment ($k_{tr}$). Kinetic data are presented as plots of $k_{tr}$ vs the isometric force developed at each pCa.

The force and kinetic data presented in the following section were obtained from each muscle preparation first during maximal activation at pCa 4.5, next during submaximal activation at a pCa>4.5, and once again during activation at pCa 4.5. The preparation was then bathed in relaxing solution containing peptide, after which the identical activation sequence was imposed. Finally, the peptide was washed out of the preparation by repeated washings in relaxing solution so that control measurements could again be done in the absence of peptide. This bracketing protocol ensured that the results in the presence of peptide were corrected for time-dependent rundown of the preparations during the experiment.

Porcine Myocardium.

Measurements of $Ca^{2+}$ sensitivity of force were also performed using skinned myocardium from pig hearts, since these hearts are more similar to human hearts with respect to protein isoform expression than are mouse hearts. Specifically, the principal myosin isoform in porcine and human hearts is the much slower β-cardiac myosin, while the principal isoform in mouse hearts is the faster α-cardiac myosin. The development of force in cardiac muscle exhibits positive cooperativity in that binding of myosin to actin enhances the activation state of the thin filament, which recruits additional myosins to bind thereby increasing force (Moss and Fitzsimons, 2010). The slower β-cardiac isoform would be predicted to have a greater activating effect on the cardiac thin filament due to the longer residency time of the slower myosin on the thin filament.

Example 2

Results

Murine Myocardium.

The peptide disruptor of MyBP-C binding to myosin (called peptide "302a") was infused into mouse skinned myocardium at a concentration of 50 µM (FIG. 1). Force at each pCa was increased by the peptide, resulting in a shift of the force-pCa relationship to lower $Ca^{2+}$ concentrations, i.e., the $pCa_{50}$ increased from level observed in the control to the level observed following peptide treatment. Treatment of the preparations with a scrambled peptide had no effect on the force-pCa relationship, indicating that the peptide is a specific activator of myocardial force.

Figure 2:
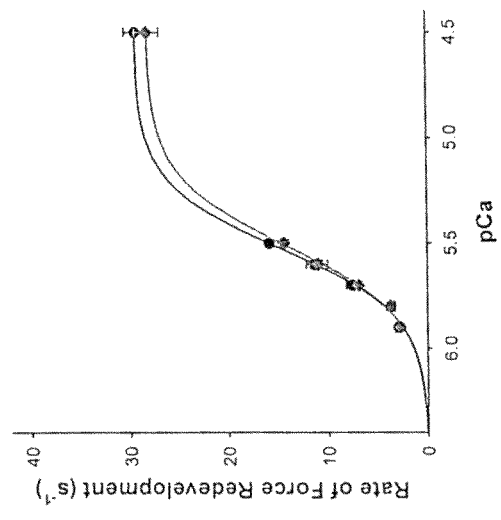
FIG. 2. Effects of peptides on the rate of force development in murine myocardium. Left panel: The rate constant of force development (ktr) was increased at each pCa studied by treatment of skinned myocardium with 50 μM 302a. Circles are control data before peptide; triangles are data following treatment with peptide 302a. Right panel: The rate of force development was unaffected by treatment with a scrambled peptide. Circles are control data before peptide; diamonds are control data following peptide treatment.
Figure 2:
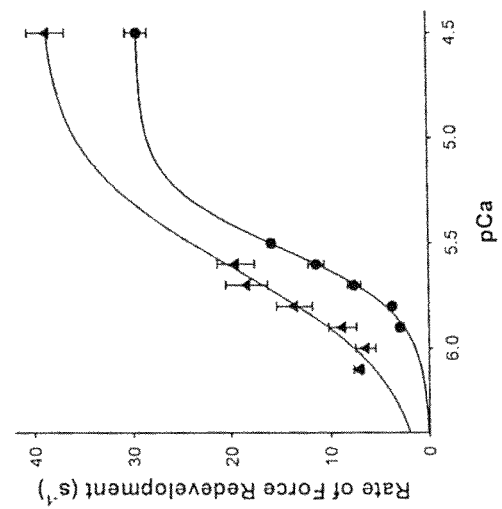
Figure 3:
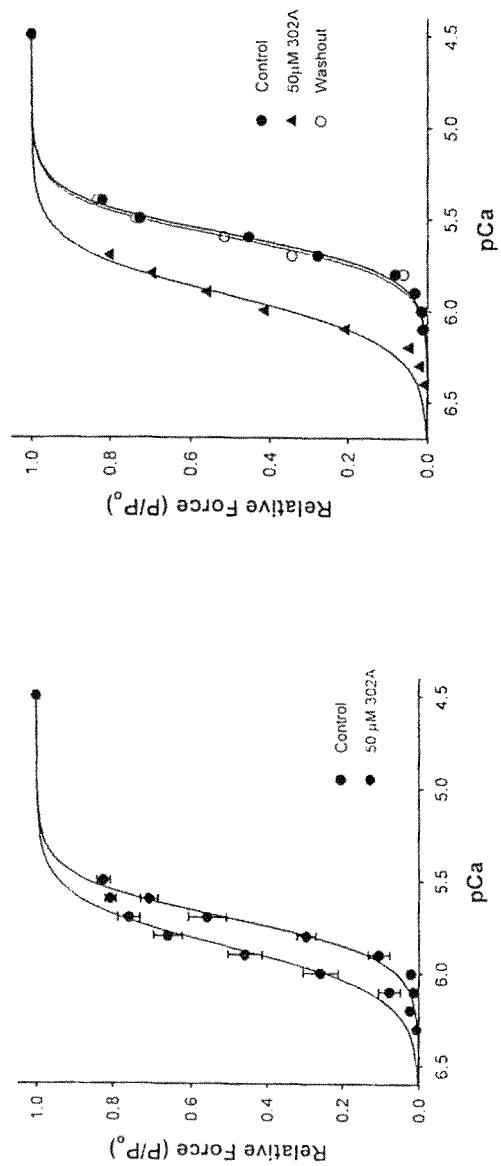
FIG. 3. Comparison of effects of peptide 302a on the $Ca^{2+}$ sensitivity of force in murine and porcine myocardium. Left panel: Treatment of mouse myocardium with 50 μM 302a increased the $Ca^{2+}$ sensitivity of force by 0.15 pCa units, i.e., $pCa_{50}$ was 5.70±0.02 in control myocardium and 5.85±0.02 following treatment with peptide. Right panel: Treatment of porcine myocardium with 50 μM 302a increased the $Ca^{2+}$ sensitivity of force by 0.32 pCa units, i.e., $pCa_{50}$ was 5.60 in control myocardium and 5.92 following treatment with peptide. Washout of the peptide reversed the effect.

Peptide 302a also accelerated the rate of force development at each pCa studied in that the ktr-pCa relationship was shifted to lower $Ca^{2+}$ concentrations when the preparation was treated with 50 µM 302a, but not when treated with scrambled peptide (FIG. 2). Consistent with this prediction, the effects of the 302a peptide on force development were significantly greater in porcine than in murine skinned myocardium (FIG. 3).

Figures 4, 5:
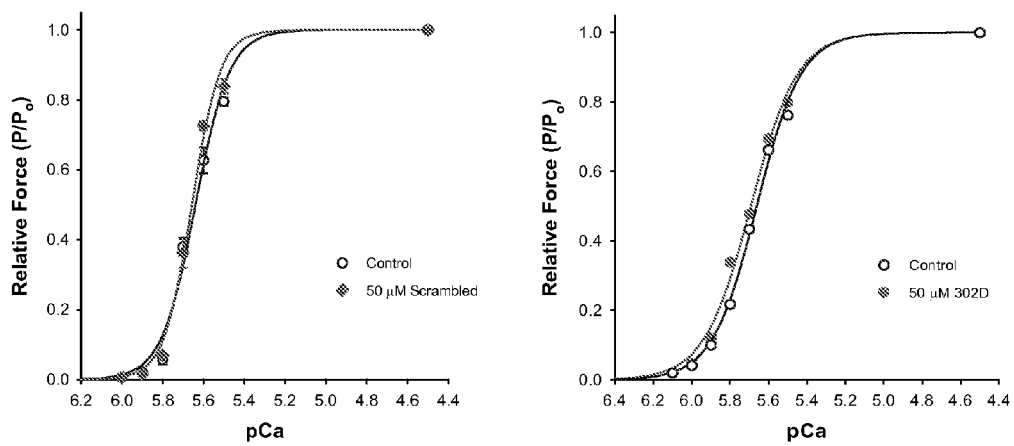
FIG. 4. Peptide variants.
FIG. 5. Non-effect of scrambled or phosphomimetic (A→D) 18-mer peptides.
Figure 6:
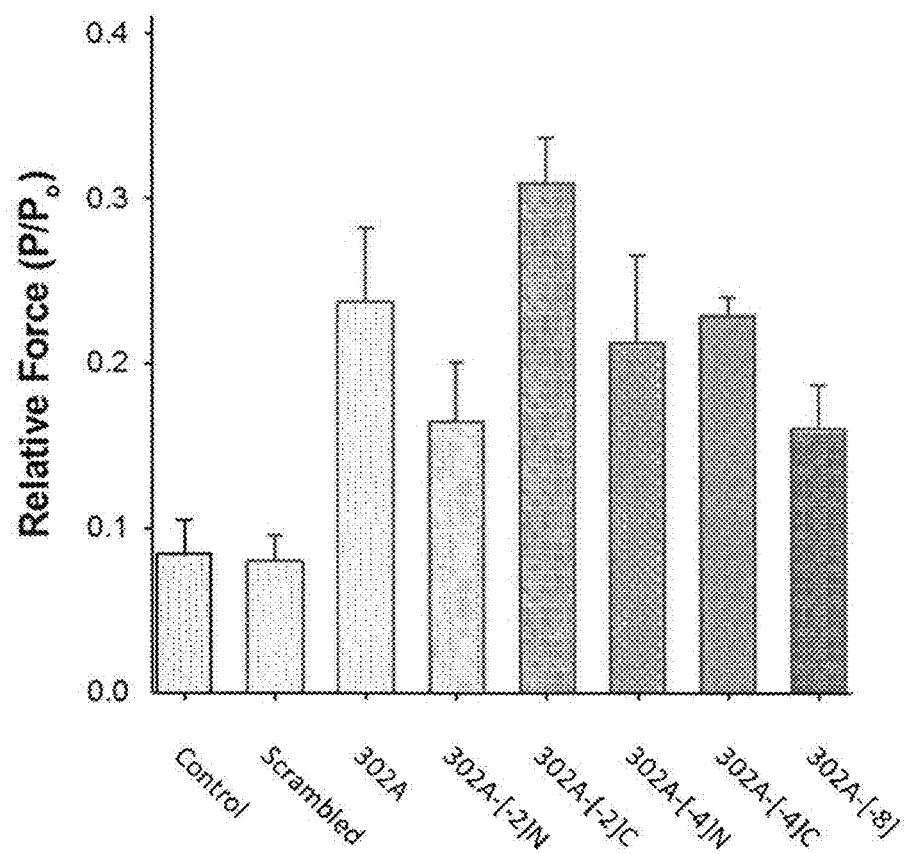
FIG. 6. Relative effects of various peptides on force at pCa 5.9 (scaled to force at pCa 4.5), mouse.
Figure 7:
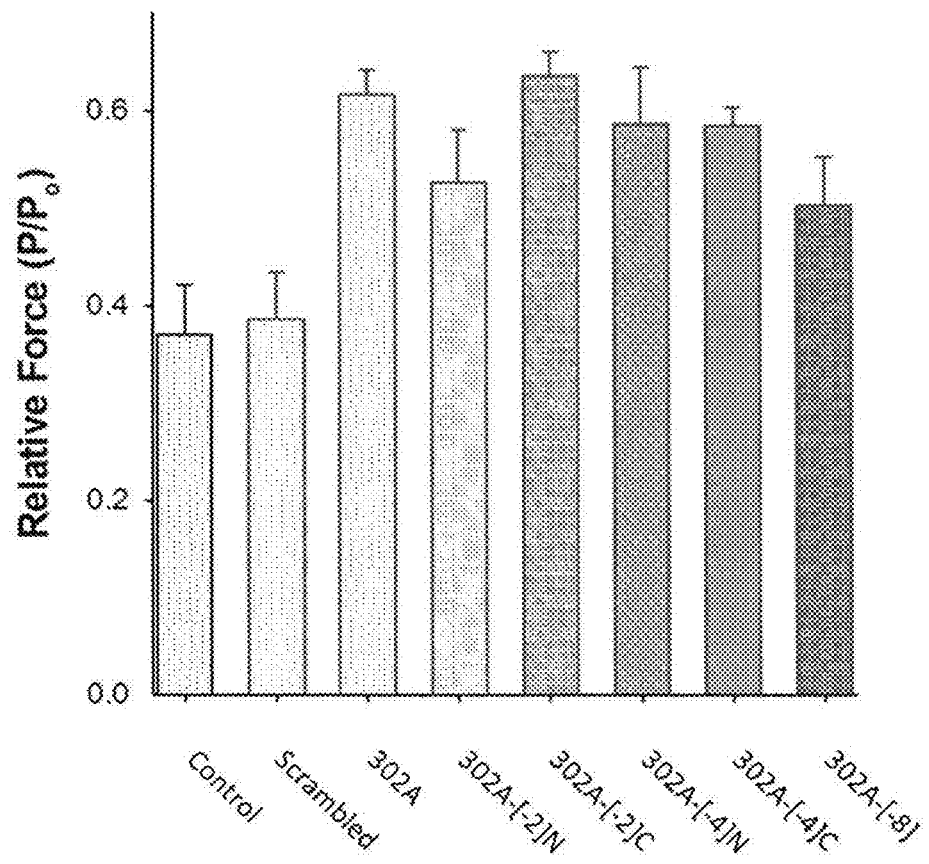
FIG. 7. Relative effects of various peptides on force at pCa 5.9 (scaled to force at pCa 4.5), mouse.

FIG. 4 shows various particular peptides used in studies shown in FIGS. 5-7. FIG. 5 show that scrambled or phosphomimetic (302A→D) 18-mer peptides have no activity at 50 µM on the force-pCa relationship. The scrambled peptide was tested on mouse myocardium using a sequence generated randomly from the 302A base peptide. The 302D peptide was tested on porcine myocardium and is a phosphomimetic that was predicted to have no effect on the force-pCa relationship, since phosphorylation of native MyBP-C in situ disrupts its interaction with myosin in vitro and in vivo. Thus, no effect is the predicted result.

FIG. 6 shows the relative effects of various peptides on force at pCa 5.9 (scaled to force at pCa 4.5) in mouse. At this high pCa (low [$Ca^{2+}$]), force in untreated skinned myocardium is ~8% of maximum force at pCa 4.5. At 50 µM, peptide 302A increases force to nearly 3×. At 50 µM, peptide 302A-[-2]C causes a further increase in force, while 302A-[-4]$_C$ mitigates this increase, i.e., has an effect approximately equal to the 302A base peptide. All peptides increased force relative to control but the increases were smaller than those observed with 302A. Thus, the 302A-[4]$_C$ (16-mer) peptide has greater effects than the 302A peptide, while the 302A-[-4]$_C$ (14-mer) peptide has effects similar to the 302A peptide. N-terminal-truncated peptides increase force but these increases are smaller than observed with the 302A peptide.

FIG. 7 showns the relative effects of various peptides on force at pCa 5.9 (scaled to force at pCa 4.5) in mouse. At this intermediate pCa, force in untreated myocardium is ~35% of maximum force at pCa 4.5. The data show that at 50 µM, peptide 302A increases force to nearly 2× control. Furthermore, truncated peptides increased force by amounts that were similar to 302A, i.e., 302A-[-2]$_C$, slightly less than 302A (302A-[-4]$_C$, 302A-[-4]$_N$) or less than 302A (302A-[-4]$_N$, 302A-[-8]). Thus, all truncated 302A peptides increased force development, but only the 302A-[-2]$_C$ (16-mer) increased force to the same extent as the full-length 302A peptide.

CONCLUSIONS

From these results, the inventors conclude that a peptide disruptor of the binding of MyBP-C to cardiac muscle increases the force developed at each concentration of free $Ca^{2+}$ tested and also increased the rate of force development. Since living myocardium operates at an intracellular $Ca^{2+}$ concentration that would elicit forces that are approximately half-maximal, the effects observed here in skinned myocardium predict that the peptide would nearly double the force and rate of force development in vivo. Also, because the force developed by myocardium is diminished in heart failure, i.e., less than half-maximal, the peptide has the potential to increase developed force several fold in failing myocardium.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VIII. REFERENCES

The following references, to the extent that they provide exemplary procedural or other details supplementary to those set forth herein, are specifically incorporated herein by reference.

U.S. Pat. No. 5,440,013
U.S. Pat. No. 5,446,128
U.S. Pat. No. 5,475,085
U.S. Pat. No. 5,597,457
U.S. Pat. No. 5,604,251
U.S. Pat. No. 5,618,914
U.S. Pat. No. 5,670,155
U.S. Pat. No. 5,672,681
U.S. Pat. No. 5,674,976
U.S. Pat. No. 5,710,245
U.S. Pat. No. 5,790,421
U.S. Pat. No. 5,840,833
U.S. Pat. No. 5,859,184
U.S. Pat. No. 5,889,155
U.S. Pat. No. 5,929,237
U.S. Pat. No. 6,093,573
U.S. Pat. No. 6,261,569
U.S. Pat. No. 7,183,059
U.S. Pat. No. 7,192,713
U.S. Publication Application No. 2005/0015232
Bodanszky et al., *J. Antibiot.*, 29(5):549-53, 1976.
Bristow, *Cardiology*, 92:3-6, 1999.
Capaldi et al., *Biochem. Biophys. Res. Comm.*, 74(2):425-433, 1977.
Chen et al., *J. Gen. Physiol.*, 136:615-627, 2010.
Cohen et al., *J. Med. Chem.*, 33:883-894, 1990.
Durand et al., *Ann. Med.*, 27:311-317, 1995.
Eichhorn and Bristow, *Circulation*, 94:2285-2296, 1996.
Fernández, *Phys. Rev. Lett.*, 108:—188102, 2012.
Fischer, *Med. Res. Rev.*, 27(6):755-796, 2007.
Gronenborn et al., *Anal. Chem.*, 62(1):2-15, 1990.
Jackson, *Seminars in Oncology*, 24:L164-172, 1997.
Johnson et al., In: *Biotechnology and Pharmacy*, Pezzuto et al., eds., Chapman and Hall, New York, 1993.

Jones et al., *J. Med. Chem.*, 39:904-917, 1996.
Klaassen, In: *The Pharmacological Basis of Therapeutics*, Goodman and Gilman, Eds., Pergamon Press, 8th Ed., 1990.
Li et al., *Gen. Inf.*, 10:30-40, 1999.
McPherson, *J. Biol. Chem.*, 251:6300-6306, 1976.
Merrifield, *J. Am. Chem. Soc.*, 85(14):2149-2154, 1963.
Moss and Fitzsmons, *J. Gen. Physiol.*, 136:21-27, 2010.
Navia et al., *Curr. Opin. Struct. Biol.*, 2:202-210, 1992.
Olsson et al., *Am. J. Physiol.*, 287:H2712-H2718, 2004.
PCT Appln. PCT/US00/03745
PCT Appln. PCT/US00/14667
PCT Appln. PCT/US99/11913
PCT Appln. PCT/US99/11913
PCT Appln. PCT/US99/18441
PCT Appln. WO 98/33791
Peptide Synthesis, 1985
Physicians Desk Reference.
Pietrosemoli et al., *J. Prot. Res.*, 6:3519-3526, 2007.
Protective Groups in Organic Chemistry, 1973
Protein NMR Spectroscopy, Principles and Practice, 1996
Remington's Pharmaceutical Sciences, 15th ed., 1035-1038 and 1570-1580, Mack Publishing Company, PA, 1980.
Schafineister et al., *J. Amer. Chem. Soc.*, 122(24):5891-5892, 2000.
Solid Phase Peptide Synthelia, 1984
Stelzer et al., *J. Gen. Physiol.*, 128:261-272, 2006.
The Merck Index, 11th Edition.
Weber, *Advances Protein Chem.*, 41:1-36, 1991.
Wider, *Bio Techniques*, 29:1278-1294, 2000.
Young et al., In: *Handbook of Applied Therapeutics*, 7.1-7.12 and 9.1-9.10, 1989.

What is claimed is:

1. A method of treating heart failure comprising:
   (a) identifying a patient exhibiting one or more symptoms of heart failure; and
   (b) administering to said patient a peptide of no more than 50 residues that comprises the MyBP-C binding site for myosin and binds to myosin and comprises the sequence LKKRDXFRRD (SEQ ID NO: 1), where X is A, V or D.

2. The method of claim 1, wherein administering the peptide is performed intramuscularly, intravenously or by direct injection into cardiac tissue.

3. The method of claim 1, wherein administering the peptide comprises oral, transdermal, sustained release, controlled release, delayed release, suppository, or sublingual administration.

4. The method of claim 1, further comprising administering to said patient a second heart failure therapy.

5. The method of claim 4, wherein said second therapy is selected from the group consisting of a beta blocker, an ionotrope, a diuretic, ACE-I, AII antagonist, BNP, or a $Ca^{++}$ channel blocker.

6. The method of claim 4, wherein said second therapy is administered at the same time as said peptide.

7. The method of claim 4, wherein said second therapy is administered either before or after said peptide.

8. The method of claim 1, wherein treating comprises improving one or more symptoms of heart failure.

9. The method of claim 8, wherein said one or more improved symptoms comprises increased exercise capacity, increased cardiac ejection volume, increased cardiac ejection fraction, decreased left ventricular end diastolic pressure, decreased pulmonary capillary wedge pressure, increased cardiac output, or cardiac index, lowered pulmonary artery pressures, decreased left ventricular end systolic and diastolic dimensions, decreased left and right ventricular wall stress, decreased wall tension, increased quality of life, and decreased disease-related morbidity or mortality.

10. The method of claim 1, wherein the peptide comprises the sequence FSSLLKKRDXFRRD (SEQ ID NO: 48), FSSLLKKRDXFRRDXK (SEQ ID NO: 49), LKKRDXFRRDXKLE (SEQ ID NO: 50), SLLKKRDXFRRDXKLE (SEQ ID NO: 51), FSSLLKKRDXFRRDXKLE (SEQ ID NO: 52), or SLLKKRDAFRRDAKLE (SEQ ID NO: 53).

11. The method of claim 1, wherein said peptide is no more than 25, 30, 35, 40 or 45 residues.

12. The method of claim 1, wherein said peptide comprises a cell penetrating domain.

13. The method of claim 1, wherein said peptide comprises some or all D-amino acids.

14. A method of slowing the progression of heart failure comprising:
   (a) identifying a patient at risk of developing severe heart failure; and
   (b) administering to said patient a peptide of no more than 50 residues that comprises the MyBP-C binding site for myosin and binds to myosin and comprises the sequence LKKRDXFRRD (SEQ ID NO: 1), where X is A, V or D.

15. The method of claim 14, wherein the patient at risk may exhibit one or more of a list of risk factors comprising long-standing uncontrolled hypertension, uncorrected valvular disease, chronic angina, recent myocardial infarction, congenital predisposition to heart disease or pathological hypertrophy.

16. The method of claim 14, wherein the patient at risk may be diagnosed as having a genetic predisposition to heart failure.

17. The method of claim 14, wherein the patient at risk may have a familial history of heart failure.

18. The method of claim 14, further comprising administering to said patient a second heart failure therapy.

19. The method of claim 18, wherein said second therapy is selected from the group consisting of a beta blocker, an ionotrope, a diuretic, ACE-I, AII antagonist, BNP, or a $Ca^{++}$ channel blocker.

20. The method of claim 14, wherein said subject is a heart transplant recipient.

21. The method of claim 14, wherein the peptide comprises the sequence FSSLLKKRDXFRRD (SEQ ID NO: 48), FSSLLKKRDXFRRDXK (SEQ ID NO: 49), LKKRDXFRRDXKLE (SEQ ID NO: 50), SLLKKRDXFRRDXKLE (SEQ ID NO: 51), FSSLLKKRDXFRRDXKLE (SEQ ID NO: 52), or SLLKKRDAFRRDAKLE (SEQ ID NO: 53).

22. The method of claim 14, wherein said peptide is no more than 25, 30, 35, 40 or 45 residues.

23. The method of claim 14, wherein said peptide comprises a cell penetrating domain.

24. The method of claim 14, wherein said peptide comprises some D-amino acids.

* * * * *

UNITED STATES PATENT AND TRADEMARK OFFICE
CERTIFICATE OF CORRECTION

PATENT NO.         : 9,051,387 B2
APPLICATION NO.    : 13/827023
DATED              : June 9, 2015
INVENTOR(S)        : Richard L. Moss and Ariel Fernandez Page 1 of 1

It is certified that error appears in the above-identified patent and that said Letters Patent is hereby corrected as shown below:

In the claims

In claim 13, column 60, line 4, delete "or all".

Signed and Sealed this
Sixth Day of October, 2015

Michelle K. Lee
*Director of the United States Patent and Trademark Office*